US012188036B2

(12) United States Patent
Kim et al.

(10) Patent No.: US 12,188,036 B2
(45) Date of Patent: Jan. 7, 2025

(54) EXPRESSION CASSETTE FOR PRODUCTION OF HIGH-EXPRESSION AND HIGH-FUNCTIONALITY TARGET PROTEIN AND USE THEREOF

(71) Applicant: CELLTRION INC., Incheon (KR)

(72) Inventors: Man Su Kim, Incheon (KR); Min Soo Kim, Incheon (KR); Jong Moon Cho, Incheon (KR); Shin Jae Chang, Incheon (KR)

(73) Assignee: CELLTRION INC., Incheon (KR)

(*) Notice: Subject to any disclaimer, the term of this patent is extended or adjusted under 35 U.S.C. 154(b) by 1165 days.

(21) Appl. No.: 16/755,453

(22) PCT Filed: Oct. 11, 2018

(86) PCT No.: PCT/KR2018/011953
§ 371 (c)(1),
(2) Date: Apr. 10, 2020

(87) PCT Pub. No.: WO2019/074292
PCT Pub. Date: Apr. 18, 2019

(65) Prior Publication Data
US 2020/0299721 A1 Sep. 24, 2020

(30) Foreign Application Priority Data
Oct. 11, 2017 (KR) .......... 10-2017-0129969

(51) Int. Cl.
*C12N 15/85* (2006.01)
*C07K 16/00* (2006.01)
*C12N 15/11* (2006.01)
*C12N 15/113* (2010.01)

(52) U.S. Cl.
CPC .......... *C12N 15/85* (2013.01); *C12N 15/111* (2013.01); *C12N 2830/42* (2013.01); *C12N 2840/44* (2013.01)

(58) Field of Classification Search
CPC .......... C12N 2830/42; C12N 2840/44; C12N 15/113; C12N 2310/14; C12N 2310/141; C12N 2330/51; C07K 2317/14; C07K 16/00
See application file for complete search history.

(56) References Cited

U.S. PATENT DOCUMENTS

| 8,309,698 B2 | 11/2012 | Koh et al. |
| 9,453,219 B2 | 9/2016 | Lin et al. |
| 2007/0134795 A1 | 6/2007 | Prentice et al. |
| 2010/0015627 A1 | 1/2010 | Beuger et al. |
| 2016/0076054 A1* | 3/2016 | Auricchio ............ A61K 48/005 435/320.1 |

FOREIGN PATENT DOCUMENTS

| KR | 10-2006-0109906 | 10/2006 |
| KR | 10-2012-0093903 | 8/2012 |
| WO | WO 2008/077545 | 7/2008 |
| WO | WO 2009/058413 | 5/2009 |
| WO | WO PCT/KR2018/011953 | 5/2019 |

OTHER PUBLICATIONS

Toro Cabrera G, Mueller C. Design of shRNA and miRNA for Delivery to the CNS. Methods Mol Biol. 2016;1382:67-80. doi: 10.1007/978-1-4939-3271-9_5. PMID: 26611579 (Year: 2016).*
Powell SK et al. Viral expression cassette elements to enhance transgene target specificity and expression in gene therapy. Discov Med. Jan. 2015;19(102):49-57. PMID: 25636961; PMCID: PMC4505817 (Year: 2015).*
Haley B. et al. Vectors and parameters that enhance the efficacy of RNAi-mediated gene disruption in transgenic Drosophila. Proc Natl Acad Sci U S A. Jun. 22, 2010;107(25):11435-40. doi: 10.1073/pnas.1006689107. Epub Jun. 4, 2010. PMID: 20534445; PMCID: PMC2895090 (Year: 2010).*
Beuger V. et al. Short-hairpin-RNA-mediated silencing of fucosyltransferase 8 in Chinese-hamster ovary cells for the production of antibodies with enhanced antibody immune effector function. Biotechnol Appl Biochem. May 2009;53(Pt 1):31-7. doi: 10.1042/BA20080220. PMID: 19032154. (Year: 2009).*
Zhang X. et al. Branch point identification and sequence requirements for intron splicing in Plasmodium falciparum. Eukaryot Cell. Nov. 2011;10(11):1422-8. doi: 10.1128/EC.05193-11. Epub Sep. 16, 2011. PMID: 21926333; PMCID: PMC3209046) (Year: 2011).*
Beuger et al., "Short-Hairpin-RNA-Mediated Silencing of Fucosyltransferase 8 in Chinese-Hamster Ovary Cells for the Production of Antibodies with Enhanced Antibody Immune Effector Function", Biotechnology and Applied Biochemistry 53, 2009, Great Britain, pp. 31-37.
Calloni et al., "Scaffolds for Artificial miRNA Expression in Animal Cells", Human Gene Therapy Methods vol. 26, No. 5, 2015, United States, 13 pages.
Hu et al., "Comparative Studies of Various Artificial microRNA Expression Vectors for RNAi in Mammalian Cells", Molecular Biotechnology 46, 2010, United States, pp. 34-40.
Xia et al., "Multiple shRNAs Expressed by an Inducible Pol II Promoter can Knock Down the Expression of Multiple Target Genes", BioTechniques vol. 41, No. 1, 2006, United States, pp. 64-68.

(Continued)

*Primary Examiner* — Amy M Bunker
(74) *Attorney, Agent, or Firm* — Wells St. John P.S.

(57) ABSTRACT

The present invention relates to an expression cassette for a target protein, comprising a promoter, a polynucleotide coding for the target protein, an intron sequence, and a poly A sequence, an expression vector, and a transformant. The expression cassette for a target protein according to the present invention can simultaneously perform the expression of the intron sequence and the target protein through one transduction and exhibits the effect of inducing the high expression and high functionality of the target protein by regulating the expression of an endogenous gene.

8 Claims, 17 Drawing Sheets

Specification includes a Sequence Listing.

(56) References Cited

OTHER PUBLICATIONS

Du et al., "Design of Expression Vectors for RNA Interference Based on miRNAs and RNA Splicing", The FEBS Journal vol. 273, 2006, United Kingdom, pp. 5421-5427.
Emmerling et al., "Temperature-Sensitive miR-483 is a Conserved Regulator of Recombinant Protein and Viral Vector Production in Mammalian Cells", Biotechnology and Bioengineering vol. 113, No. 4, Apr. 2016, Germany, pp. 830-841.
Fischer et al., "miR-2861 as Novel HDAC5 Inhibitor in CHO Cells Enhances Productivity While Maintaining Product Quality", Biotechnology and Bioengineering vol. 112, No. 10, Oct. 2015, Germany, pp. 2142-2153.
Hong et al., "A Novel RNA Silencing Vector to Improve Antigen Expression and Stability in Chinese Hamster Ovary Cells", Vaccine vol. 25, 2007, Netherlands, pp. 4103-4111.
Kang et al., "A Single-Plasmid Vector for Transgene Amplification using Short Hairpin RNA Targeting the 3'-UTR of Amplifiable dhfr", Applied Microbiology and Biotechnology vol. 99, 2015, Germany, pp. 10117-10126.
Wu et al., "Short Hairpin RNA Targeted to Dihydrofolate Reductase Enhances the Immunoglobulin G Expression in Gene-Amplified Stable Chinese Hamster Ovary Cells", Vaccine vol. 26, 2008, Netherlands, pp. 4969-4974.
Wu, "RNA Interface Technology to Improve Recombinant Protein Production in Chinese Hamster Ovary Cells", Biotechnology Advances vol. 27, 2009, United States, pp. 417-722.
Zhou et al., "Decreasing Lactate Level and Increasing Antibody Production in Chinese Hamster Ovary Cells (CHO) by Reducing the Expression of Lactate Dehydrogenase and Pyruvate Dehydrogenase Kinases", Journal of Biotechnology vol. 153, 2011, Netherlands, pp. 27-34.
Devany et al., "Intronic Cleavage and Polyadenylation Regulates Gene Expression during DNA Damage Response through U1 snRNA", Cell Discovery vol. 2, No. 16013, 2016, United Kingdom, 14 pages.
Oswald et al., "Control of Endrogenous Gene Expression Timing by Introns", Genome Biology vol. 12, No. 3, 2011, United Kingdom, 3 pages.

\* cited by examiner

```
                        SEQUENCE LISTING

<160> NUMBER OF SEQ ID NOS: 48

<210> SEQ ID NO 1
<211> LENGTH: 59
<212> TYPE: DNA
<213> ORGANISM: Artificial Sequence
<220> FEATURE:
<223> OTHER INFORMATION: Artificial Sequence

<400> SEQUENCE: 1
attacatacc agctttctgg cgttttggcc actgactgac gccagaaatg gtatgtaat        59

<210> SEQ ID NO 2
<211> LENGTH: 59
<212> TYPE: DNA
<213> ORGANISM: Artificial Sequence
<220> FEATURE:
<223> OTHER INFORMATION: Articficial Sequence

<400> SEQUENCE: 2
aactctggtc caaagaagca tgttttggcc actgactgac atgcttctgg accagagtt        59

<210> SEQ ID NO 3
<211> LENGTH: 59
<212> TYPE: DNA
<213> ORGANISM: Artificial Sequence
<220> FEATURE:
<223> OTHER INFORMATION: Artificial

<400> SEQUENCE: 3
aataacagta ccatcctttc ggttttggcc actgactgac cgaaggagt actgttatt         59
```

<210> SEQ ID NO 4
<211> LENGTH: 59
<212> TYPE: DNA
<213> ORGANISM: Artificial Sequence
<220> FEATURE:
<223> OTHER INFORMATION: Syntheticl

<400> SEQUENCE: 4
attccataca gtatcactgt cgttttggcc actgactgac gacagtgact gtatggaat      59

<210> SEQ ID NO 5
<211> LENGTH: 59
<212> TYPE: DNA
<213> ORGANISM: Artificial Sequence
<220> FEATURE:
<223> OTHER INFORMATION: Synthetic

<400> SEQUENCE: 5
tttgctgtca cactatagtc tgttttggcc actgactgac agactatagt gacagcaaa      59

<210> SEQ ID NO 6
<211> LENGTH: 59
<212> TYPE: DNA
<213> ORGANISM: Artificial Sequence
<220> FEATURE:
<223> OTHER INFORMATION: Synthetic

<400> SEQUENCE: 6
aattgcagcc actcccaata agttttggcc actgactgac ttattgggtg gctgcaatt      59

<210> SEQ ID NO 7
<211> LENGTH: 58
<212> TYPE: DNA
<213> ORGANISM: Artificial Sequence
<220> FEATURE:
<223> OTHER INFORMATION: Synthetic

<400> SEQUENCE: 7
gttagagtca ccttcacaac agttttggcc actgactgac tgttgtgagt gactctaa       58

<210> SEQ ID NO 8
<211> LENGTH: 59
<212> TYPE: DNA
<213> ORGANISM: Artificial Sequence
<220> FEATURE:
<223> OTHER INFORMATION: Synthetic

<400> SEQUENCE: 8
cgttcttgcc gatgcccata tgttttggcc actgactgac atatgggccg gcaagaacg      59

<210> SEQ ID NO 9
<211> LENGTH: 59
<212> TYPE: DNA
<213> ORGANISM: Artificial Sequence
<220> FEATURE:
<223> OTHER INFORMATION: Synthetic

<400> SEQUENCE: 9
tttatctgct aactctggtt ggttttggcc actgactgac caaccagata gcagataaa      59

<210> SEQ ID NO 10
<211> LENGTH: 59
<212> TYPE: DNA
<213> ORGANISM: Artificial Sequence
<220> FEATURE:
<223> OTHER INFORMATION: Synthetic

<400> SEQUENCE: 10
tccaaaccat gtccactttg tgttttggcc actgactgac ataaagtgca tggtttgga    59

<210> SEQ ID NO 11
<211> LENGTH: 58
<212> TYPE: DNA
<213> ORGANISM: Artificial Sequence
<220> FEATURE:
<223> OTHER INFORMATION: Synthetic

<400> SEQUENCE: 11
aagacgggag aagagaaggg agttggtttt gggtgcctca ctcctcccct cccgtctt    58

<210> SEQ ID NO 12
<211> LENGTH: 38
<212> TYPE: DNA
<213> ORGANISM: Artificial Sequence
<220> FEATURE:
<223> OTHER INFORMATION: synthetic

<400> SEQUENCE: 12
aggtgagcgg ctggaggctt gctgaaggct gtatgctg    38

<210> SEQ ID NO 13
<211> LENGTH: 37
<212> TYPE: DNA
<213> ORGANISM: Artificial Sequence
<220> FEATURE:
<223> OTHER INFORMATION: synthetic

<400> SEQUENCE: 13
aggtgagcgg agacctgagt gtgtggggga gagaagg    37

<210> SEQ ID NO 14
<211> LENGTH: 30
<212> TYPE: DNA
<213> ORGANISM: Artificial Sequence
<220> FEATURE:
<223> OTHER INFORMATION: synthetic

<400> SEQUENCE: 14
gtgctgaatc gataggtgag cggctggagg    30

<210> SEQ ID NO 15
<211> LENGTH: 17
<212> TYPE: DNA
<213> ORGANISM: Artificial Sequence
<220> FEATURE:
<223> OTHER INFORMATION: synthetic

<400> SEQUENCE: 15
aggtgagcgg ctggagg    17

<210> SEQ ID NO 16
<211> LENGTH: 7
<212> TYPE: DNA
<213> ORGANISM: Artificial Sequence
<220> FEATURE:
<223> OTHER INFORMATION: synthetic

<400> SEQUENCE: 16 tgctaac    7

<210> SEQ ID NO 17

```
<211> LENGTH: 7
<212> TYPE: DNA
<213> ORGANISM: Artificial Sequence
<220> FEATURE:
<223> OTHER INFORMATION: synthetic

<400> SEQUENCE: 17 ctcctac                                                                          7

<210> SEQ ID NO 18
<211> LENGTH: 7
<212> TYPE: DNA
<213> ORGANISM: Artificial Sequence
<220> FEATURE:
<223> OTHER INFORMATION: synthetic

<400> SEQUENCE: 18 gcctcac                                                                          7

<210> SEQ ID NO 19
<211> LENGTH: 30
<212> TYPE: DNA
<213> ORGANISM: Artificial Sequence
<220> FEATURE:
<223> OTHER INFORMATION: synthetic

<400> SEQUENCE: 19
catgttcatg ccttcttctt tttcctacag                                                 30

<210> SEQ ID NO 20
<211> LENGTH: 45
<212> TYPE: DNA
<213> ORGANISM: Artificial Sequence
<220> FEATURE:
<223> OTHER INFORMATION: synthetic

<400> SEQUENCE: 20
catgttcatg ccttcttctt tttcctacag ctcctgggca acgtg                                45

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
cctatcttcc ctgtctcagc tcag                                                       24

<210> SEQ ID NO 22
<211> LENGTH: 34
<212> TYPE: DNA
<213> ORGANISM: Artificial Sequence
<220> FEATURE:
<223> OTHER INFORMATION: synthetic

<400> SEQUENCE: 22
cctatcttcc ctgtctcagc tcagtgctgg gggt                                            34

<210> SEQ ID NO 23
<211> LENGTH: 181
<212> TYPE: DNA
<213> ORGANISM: Artificial Sequence
<220> FEATURE:
<223> OTHER INFORMATION: synthetic

<400> SEQUENCE: 23
```

```
aggtgagcgg agccaggagt ggtggctcat gtctgtaatt ccagcacttg agaggtagaa      60
gtgggaggac tgcttgagct caagagtttg atattatcct ggacaacata gcaagacctc    120
gtctctactt aaaaaaaaaa aatttgctaa ccatgttcat gccttcttct ttttcctaca    180
g                                                                   181
```

```
<210> SEQ ID NO 24
<211> LENGTH: 194
<212> TYPE: DNA
<213> ORGANISM: Artificial Sequence
<220> FEATURE:
<223> OTHER INFORMATION: synthetic

<400> SEQUENCE: 24
aggtgagcgg ctggaggctt gctgaaggct gtatgctgat tacataccag ctttctggcg     60
ttttggccac tgactgacgc cagaaatggt atgtaatcag gacacaaggc ctgttactag    120
cactcacatg gaacaaatgg cctgctaacc atgttcatgc cttcttcttt ttcctacagc    180
tcctgggcaa cgtg                                                     194
```

```
<210> SEQ ID NO 25
<211> LENGTH: 194
<212> TYPE: DNA
<213> ORGANISM: Artificial Sequence
<220> FEATURE:
<223> OTHER INFORMATION: synthetic

<400> SEQUENCE: 25
aggtgagcgg ctggaggctt gctgaaggct gtatgctgaa ctctggtcca agaagcatg      60 ttttggccac tgactgacat gcttctggac cagagttcag gacacaaggc ctgttactag    120
cactcacatg gaacaaatgg cctgctaacc atgttcatgc cttcttcttt ttcctacagc    180
tcctgggcaa cgtg                                                     194
```

```
<210> SEQ ID NO 26
<211> LENGTH: 194
<212> TYPE: DNA
<213> ORGANISM: Artificial Sequence
<220> FEATURE:
<223> OTHER INFORMATION: synthetic

<400> SEQUENCE: 26
aggtgagcgg ctggaggctt gctgaaggct gtatgctgaa taacagtacc atcctttcgg     60
ttttggccac tgactgaccg aaaggagtac tgttattcag gacacaaggc ctgttactag    120
cactcacatg gaacaaatgg cctgctaacc atgttcatgc cttcttcttt ttcctacagc    180
tcctgggcaa cgtg                                                     194
```

```
<210> SEQ ID NO 27
<211> LENGTH: 194
<212> TYPE: DNA
<213> ORGANISM: Artificial Sequence
<220> FEATURE:
<223> OTHER INFORMATION: synthetic

<400> SEQUENCE: 27
aggtgagcgg ctggaggctt gctgaaggct gtatgctgat tccatacagt atcactgtcg     60
ttttggccac tgactgacga cagtgactgt atggaatcag gacacaaggc ctgttactag    120
cactcacatg gaacaaatgg cctgctaacc atgttcatgc cttcttcttt ttcctacagc    180
```

```
tcctgggcaa cgtg                                                        194
```

<210> SEQ ID NO 28
<211> LENGTH: 194
<212> TYPE: DNA
<213> ORGANISM: Artificial Sequence
<220> FEATURE:
<223> OTHER INFORMATION: synthetic

<400> SEQUENCE: 28

```
aggtgagcgg ctggaggctt gctgaaggct gtatgctgtt tgctgtcaca ctatagtctg     60
ttttggccac tgactgacag actatagtga cagcaaacag gacacaaggc ctgttactag    120
cactcacatg gaacaaatgg cctgctaacc atgttcatgc cttcttcttt ttcctacagc    180
tcctgggcaa cgtg                                                      194
```

<210> SEQ ID NO 29
<211> LENGTH: 194
<212> TYPE: DNA
<213> ORGANISM: Artificial Sequence
<220> FEATURE:
<223> OTHER INFORMATION: synthetic

<400> SEQUENCE: 29

```
aggtgagcgg ctggaggctt gctgaaggct gtatgctgaa ttgcagccac tcccaataag     60
ttttggccac tgactgactt attgggtggc tgcaattcag gacacaaggc ctgttactag    120
cactcacatg gaacaaatgg cctgctaacc atgttcatgc cttcttcttt ttcctacagc    180
tcctgggcaa cgtg                                                      194
```

<210> SEQ ID NO 30
<211> LENGTH: 194
<212> TYPE: DNA
<213> ORGANISM: Artificial Sequence
<220> FEATURE:
<223> OTHER INFORMATION: synthetic

<400> SEQUENCE: 30

```
aggtgagcgg ctggaggctt gctgaaggct gtatgctggt tagagtcacc ttcacaacag     60
ttttggccac tgactgactg ttgtgagtga ctctaaccag gacacaaggc ctgttactag    120
cactcacatg gaacaaatgg cctgctaacc atgttcatgc cttcttcttt ttcctacagc    180
tcctgggcaa cgtg                                                      194
```

<210> SEQ ID NO 31
<211> LENGTH: 194
<212> TYPE: DNA
<213> ORGANISM: Artificial Sequence
<220> FEATURE:
<223> OTHER INFORMATION: synthetic

<400> SEQUENCE: 31

```
aggtgagcgg ctggaggctt gctgaaggct gtatgctgcg ttcttgccga tgcccatatg     60
ttttggccac tgactgacat atgggccggc aagaacgcag gacacaaggc ctgttactag    120
cactcacatg gaacaaatgg cctgctaacc atgttcatgc cttcttcttt ttcctacagc    180
tcctgggcaa cgtg                                                      194
```

<210> SEQ ID NO 32
<211> LENGTH: 194
<212> TYPE: DNA
<213> ORGANISM: Artificial Sequence
<220> FEATURE:
<223> OTHER INFORMATION: synthetic

<400> SEQUENCE: 32

```
aggtgagcgg ctggaggctt gctgaaggct gtatgctgtt tatctgctaa ctctggttgg      60
ttttggccac tgactgacca accagatagc agataaacag gacacaaggc ctgttactag     120
cactcacatg gaacaaatgg cctgctaacc atgttcatgc cttcttcttt tcctacagc     180
tcctgggcaa cgtg                                                       194
```

<210> SEQ ID NO 33
<211> LENGTH: 194
<212> TYPE: DNA
<213> ORGANISM: Artificial Sequence
<220> FEATURE:
<223> OTHER INFORMATION: synthetic

<400> SEQUENCE: 33

```
aggtgagcgg ctggaggctt gctgaaggct gtatgctgtc caaaccatgt ccactttatg      60
ttttggccac tgactgacat aaagtgcatg gtttggacag gacacaaggc ctgttactag     120
cactcacatg gaacaaatgg cctgctaacc atgttcatgc cttcttcttt tcctacagc     180
tcctgggcaa cgtg                                                       194
```

<210> SEQ ID NO 34
<211> LENGTH: 141
<212> TYPE: DNA
<213> ORGANISM: Artificial Sequence
<220> FEATURE:
<223> OTHER INFORMATION: synthetic

<400> SEQUENCE: 34

```
aggtgagcgg agacctgagt gtgtggggga gagaaggaag acgggagaag agaagggagt      60
tggttttggg tgcctcactc ctcccctccc gtcttgttct ctcctaccct atcttccctg     120
tctcagctca gtgctggggg t                                               141
```

<210> SEQ ID NO 35
<211> LENGTH: 193
<212> TYPE: DNA
<213> ORGANISM: Artificial Sequence
<220> FEATURE:
<223> OTHER INFORMATION: synthetic

<400> SEQUENCE: 35

```
aggtgagcgg agacctgagt gtgtggggga gagaaggaag acgggagaag agaagggagt      60
tggttttggg tgcctcactc ctcccctccc gtcttgttct ctcctaccct atcttccctg     120
tctcagctca gtgctggggg ttgctaacca tgttcatgcc ttcttctttt cctacagct     180
cctgggcaac gtg                                                        193
```

<210> SEQ ID NO 36
<211> LENGTH: 193
<212> TYPE: DNA
<213> ORGANISM: Artificial Sequence
<220> FEATURE:
<223> OTHER INFORMATION: synthetic

<400> SEQUENCE: 36

```
aggtgagcgg ctggaggctt gctgaaggct gtatgctgaa gacgggagaa gagaagggag      60
ttggttttgg gtgcctcact cctcccctcc cgtcttcagg acacaaggcc tgttactagc     120
```

```
actcacatgg aacaaatggc ctgctaacca tgttcatgcc ttcttctttt tcctacagct    180
cctgggcaac gtg                                                       193

<210> SEQ ID NO 37
<211> LENGTH: 21
<212> TYPE: DNA
<213> ORGANISM: Artificial Sequence
<220> FEATURE:
<223> OTHER INFORMATION: synthetic

<400> SEQUENCE: 37
gtggaatcta ctggcgtctt c                                              21

<210> SEQ ID NO 38
<211> LENGTH: 20
<212> TYPE: DNA
<213> ORGANISM: Artificial Sequence
<220> FEATURE:
<223> OTHER INFORMATION: synthetic

<400> SEQUENCE: 38
tcttggttca cacccatcac                                                20

<210> SEQ ID NO 39
<211> LENGTH: 22
<212> TYPE: DNA
<213> ORGANISM: Artificial Sequence
<220> FEATURE:
<223> OTHER INFORMATION: synthetic

<400> SEQUENCE: 39
cgtggaatac ctaacagcct tc                                             22

<210> SEQ ID NO 40
<211> LENGTH: 20
<212> TYPE: DNA
<213> ORGANISM: Artificial Sequence
<220> FEATURE:
<223> OTHER INFORMATION: synthetic

<400> SEQUENCE: 40
tccttcgaca gcatcaaacc                                                20

<210> SEQ ID NO 41
<211> LENGTH: 20
<212> TYPE: DNA
<213> ORGANISM: Artificial Sequence
<220> FEATURE:
<223> OTHER INFORMATION: synthetic

<400> SEQUENCE: 41
gacttggccg agagcataat                                                20

<210> SEQ ID NO 42
<211> LENGTH: 19
<212> TYPE: DNA
<213> ORGANISM: Artificial Sequence
<220> FEATURE:
<223> OTHER INFORMATION: synthetic

<400> SEQUENCE: 42
agggacactg aggaagaca                                                 19

<210> SEQ ID NO 43
<211> LENGTH: 20
```

```
<212> TYPE: DNA
<213> ORGANISM: Artificial Sequence
<220> FEATURE:
<223> OTHER INFORMATION: synthetic

<400> SEQUENCE: 43
acatctgtga ccgccattac                                              20

<210> SEQ ID NO 44
<211> LENGTH: 20
<212> TYPE: DNA
<213> ORGANISM: Artificial Sequence
<220> FEATURE:
<223> OTHER INFORMATION: synthetic

<400> SEQUENCE: 44
caatgcctgg caggataaga                                              20

<210> SEQ ID NO 45
<211> LENGTH: 23
<212> TYPE: DNA
<213> ORGANISM: Artificial Sequence
<220> FEATURE:
<223> OTHER INFORMATION: synthetic

<400> SEQUENCE: 45
ggagttccat gagaagagtt cag                                          23

<210> SEQ ID NO 46
<211> LENGTH: 21
<212> TYPE: DNA
<213> ORGANISM: Artificial Sequence
<220> FEATURE:
<223> OTHER INFORMATION: synthetic

<400> SEQUENCE: 46
gccattgtag ggaccacatt a                                            21

<210> SEQ ID NO 47
<211> LENGTH: 22
<212> TYPE: DNA
<213> ORGANISM: Artificial Sequence
<220> FEATURE:
<223> OTHER INFORMATION: synthetic

<400> SEQUENCE: 47
ccaggccatc tcagactctt tg                                           22

<210> SEQ ID NO 48
<211> LENGTH: 22
<212> TYPE: DNA
<213> ORGANISM: Artificial Sequence
<220> FEATURE:
<223> OTHER INFORMATION: synthetic

<400> SEQUENCE: 48
tgggaagaac gtgtcagttt ca                                           22
```

EXPRESSION CASSETTE FOR PRODUCTION OF HIGH-EXPRESSION AND HIGH-FUNCTIONALITY TARGET PROTEIN AND USE THEREOF

RELATED PATENT DATA

This application is a 35 U.S.C. § 371 of and claims priority to PCT International Application No. PCT/KR2018/0011953, filed 11 Oct. 2018, which claims priority to KR Application No. 10-2017-0129969, filed 11 Oct. 2017, and the teachings of which are incorporated herein by reference.

TECHNICAL FIELD

The present invention relates to an expression cassette for production of a high-expression and high-functionality target protein including a promoter and to the use thereof.

This patent incorporates by reference the material in the sequence listing.txt file submitted in computer readable form. The text file is titled HA153seqlist_ST25.txt. This file was created Jun. 2, 2020 and is 13 KB.

BACKGROUND ART

Animal cells, such as Chinese hamster ovary (CHO) cells, are widely used industrially for the production of recombinant proteins, particularly therapeutic proteins such as antibodies. Proteins produced using mammalian cells such as CHO cells are subjected to post-translational modification and then glycosylation to realize complete biological activity.

Although production of recombinant proteins using mammalian cells such as CHO cells enables high-concentration production due to improvement in expression vectors, expression methods, culture techniques, etc. compared to the past, expensive media are used, and moreover, the growth rate is slow, resulting in high production costs compared to production using microorganisms or yeast. Therefore, in the production of recombinant proteins using mammalian cells, it is necessary from a commercial point of view to increase productivity as much as possible.

Moreover, when an animal cell line in which the expression of a specific endogenous gene is regulated is used for the production of recombinant proteins, particularly therapeutic antibodies, it may be very efficiently employed in improving productivity or therapeutic effects and broadening the scope of treatment.

For example, it has been reported for an IgG-type therapeutic antibody that, when fucose is absent in the glycan attached to asparagine 297 of the Fc region, the binding force of the natural killer cell to the antibody Fc region receptor is enhanced, thus increasing antibody-dependent cellular cytotoxicity (ADCC) (Shields, R. L. et al., The Journal of Biological Chemistry, 277 (30), 26733-26740, 2002). Therefore, when the enzyme that attaches fucose to asparagine 297 of the Fc region of the antibody is inhibited, a therapeutic antibody having high antibody-dependent cytotoxicity may be produced.

In order to increase the productivity of a recombinant protein and control the quality thereof, there is a method of regulating the expression of a specific endogenous gene. Examples of the method of inhibiting the expression of an endogenous gene may include gene knockout due to homologous recombination (Yamane-Ohnuki, N. et al., Biotechnology and Bioengineering, 87 (5), 614-622, 2004), RNA interference that induces mRNA decomposition of a target gene using RNA that has a sequence complementary to the mRNA of the target gene (Mori, K. et al., Biotechnology and Bioengineering, 88 (7), 901-908, 2004), and the like, and a method of increasing the expression of an endogenous gene may include a method of inducing high expression via the transfection of a specific endogenous gene having a strong promoter. Moreover, small-sized micro RNA (miRNA) that is transcribed from noncoding DNA is known to have a biological function of regulating the translation of proteins and is thus reported as a new regulator that regulates cell function and fate, and research results have been reported to control cell proliferation and death by regulating the expression of an endogenous gene in the post-transcriptional regulation process using such miRNA (Amelia Cimmino et al., PNAS, 102 (39), 13944-13949, 2005).

In order to regulate the expression of a specific endogenous gene by the above method, an expression vector having genetic information capable of regulating the expression of a specific endogenous gene is required, and a cell line in which the endogenous gene is stably increased or suppressed through transfection into animal cells should be selected. In order to select such a cell line, a vector having endogenous gene regulation information also includes genetic information of a selection maker. A cell line in which the expression of a specific endogenous gene is regulated is first manufactured and then additionally transfected with an expression vector for the expression of a recombinant protein, and a recombinant protein expression cell line is selected using a different type of selection marker from the one contained in the vector for regulating the expression of a specific endogenous gene. Because of this process complexity, it is more difficult to produce a recombinant protein while simultaneously regulating the expression of multiple endogenous genes.

As an additional method of increasing the productivity of the recombinant protein, there may be the use of an intron structure. Intron, which is a sequence found in eukaryotic cells, is a sequence removed during the process in which precursor mRNA (pre-mRNA) transcribed by an RNA polymerase is processed into mature RNA through a splicing process, and it has been reported that protein expression is improved through a splicing process induced using an intron. (Herve' Le Hir. et al., Trends in Biochemical Sciences, 28 (4), 215-220, 2003).

Therefore, in order to overcome existing difficulties that occur when simultaneously regulating multiple endogenous genes, the present inventors have invented a vector in which intronized short hairpin RNA (shRNA) sequences that regulate the expression of endogenous genes and a target recombinant protein sequence are transcribed and expressed with a single promoter, thus culminating in the present invention, capable of inducing the high expression and high functionality of a recombinant protein by regulating the expression of multiple endogenous genes through a single transfection.

DISCLOSURE

Technical Problem

Upon conventional endogenous gene expression regulation and target protein production, respective expression cassettes are used, making it difficult to select cell lines and to appropriately regulate the expression of endogenous genes.

An objective of the present invention is to provide a target protein expression cassette including a promoter, a polynucleotide coding for the target protein, a polynucleotide sequence encoding an intronic RNA sequence and a poly A sequence in order to produce a high-expression and high-functionality target protein.

Another objective of the present invention is to provide a vector including the expression cassette for production of a target protein.

Still another objective of the present invention is to provide a transformant including the expression cassette for production of a target protein.

Yet another objective of the present invention is to provide a method of manufacturing a target protein including culturing a transformant including the expression cassette for production of a target protein.

Technical Solution

The present invention provides an expression cassette for production of a target protein, which is a target protein expression cassette including a promoter, a polynucleotide coding for the target protein, a polynucleotide sequence encoding_an intronic RNA sequence and a poly A sequence, in which the intronic RNA sequence includes a splicing donor, a branch and a splicing acceptor.

In an embodiment of the present invention, the target protein may be an antibody or a fragment thereof.

In an embodiment of the present invention, at least one intronic RNA sequence may be present on a single target protein expression cassette.

In an embodiment of the present invention, a polynucleotide sequence encoding at least one intronic RNA sequence may be present on a single target protein expression cassette.

In an embodiment of the present invention, the expression cassette may include a polynucleotide sequence encoding at least one intronic RNA sequence selected from the group consisting of: a) a polynucleotide sequence encoding at least one intronic RNA sequence located between a promoter and a polynucleotide coding for the target protein; b) a polynucleotide sequence encoding at least one intronic RNA sequence located between a polynucleotide coding for the target protein and a poly A; and c) a polynucleotide sequence encoding at least one intronic RNA sequence located between a promoter and a polynucleotide coding for the target protein and a polynucleotide sequence encoding at least one intronic RNA sequence located between a polynucleotide coding for the target protein and a poly A.

In an embodiment of the present invention, the intronic RNA sequence may further include an RNA sequence for target gene expression regulation.

In an embodiment of the present invention, the target gene may be at least one selected from the group consisting of FUT8 (Alpha-1,6-fucosyltransferase), HDAC5 (Histone Deacetylase 5), LDHA (Lactate dehydrogenase A), CXCR4 (C—X—C chemokine receptor type 4), DHFR (Dihydrofolate reductase), PDK4 (Pyruvate dehydrogenase lipoamide kinase isozyme 4), MAPK3 (Mitogen-activated protein kinase 3), KANK4 (KN Motif And Ankyrin Repeat Domains 4), PDI (Protein disulfide isomerase), CNX (Calnexin), CRT (Calreticulin), eIF2alpha (Non-phosphorylatable version of the eukaryotic translation initiation factor 2 alpha), ZFP-TF (Artificial zinc finger protein transcription factor), ATF4 (Activating transcription factor 4), GADD34 (Growth arrest and DNA damage inducible protein 34), mTOR (Mammalian target of rapamycin), BIP (Heat shock 70 kDa protein 5), ATF6C (Activating transcription factor 6C), XBP1 (X-box binding protein 1), BCL2 (B-cell lymphoma 2), BCLxL (BCL2-like 1), Mutated form of BCL-xL (Asp29Asn variant), XIAP (X-linked inhibitor of apoptosis), a mutant form of XIAREAX197), AVEN (Apoptosis, caspase inhibitor), C-MYC (Myelocytomatosis oncogene), FAIM (Fas apoptotic inhibitory molecule), 30Kc6 (Apoptosis-inhibiting 30K protein), TERT (Telomerase reverse transcriptase), E1B-19K (Control protein E1B 19K), MDM2 (Murine double-mutant 2), E2F1 (E2F transcription factor 1), HSP27 (Heat shock proteins 27), HSP70 (Heat shock proteins 70), MCL1 (Myeliod cell leukemia 1), AKT1 (RAC-alpha serine/threonineprotein kinase), Beclin-1, ST6GAL (Alpha 2,6 sialyltransferase), GnT-IV (Alpha-1,3-D-mannoside beta 1,4 Nacetylglucosaminyltransferase), GnT-V (alpha 1,6 Dmannoside beta-1,6 Nacetylglucosaminyltransferase), ST3GAL (Alpha 2,3 sialyltransferase), GalT (beta 1,4 galactosyltransferase), CMP-SAT (CMP-sialic acid transporter), CMP-SAS (CMP-sialic acid synthetase), GNE (Mutant uridine diphosphate-N-acetyl glucosamine 2-epimerase), GnT-III (Beta 1,4 Nacetylglucosaminyltransferase III), ManII (Golgi alpha-mannosidase II), C2GnT (Beta 1,6 Nacetylglucosaminyltransferase), RMD (GDP-6-deoxy-d-lyxo-4-hexulose reductase), VHb (*Vitreoscilla* hemoglobin), CPS Karbamoyl phosphate synthetase I), OTC (Ornithine transcarbamoylase), PC (Pyruvate carboxylase), GLUT5 (Glucose transporter protein 5), MDH2 (Malate dehydrogenase II), TAUT (Taurine transporter), ALT1 (Alanine aminotransferase 1), XBP1 (X-box binding protein 1), XBP1s (Spliced form of XBP-1), SLY1 (Suppressor of loss of YPT1 protein 1), MUNC18C (syntaxin binding protein 3), CERT (Ceramide transfer protein), Mutant form of CERT (S132A), SNAP-23 (Synaptosome-associated protein of 23 kDa), VAMP8 (Vesicle-associated membrane protein 8), SRP14 (Human signaling receptor protein 14), p21CIP1 (Cyclin-dependent kinase Inhibitor 1A), C/EBP-alpha (CCAAT/enhancer-binding protein alpha), p27KIP1 (Cyclin-dependent kinase inhibitor 1B), CDKL3 (Cyclin-dependent kinase like 3), COX15 (Cytochrome c oxidase subunit), VCP (Valosin-containing protein), BAX (BCL2-associated X protein), BAK (BCL2-antagonist/killer), GS (Glutamine synthetase), MGAT1 (N-acetylglucosaminyltransferase 1), SLC35C1 (GDP-fucose transporter), SLC35A1 (CMPsialic acid transporter), B4GALT1 (Beta 1,4 galactosyltransferase 1), B3GNT2 (Beta 1,3 Nacetylglucosaminyltransferase 2), PAM (Peptidylglycine alphaamidating monooxygenase), Caspase 3, Caspase 7, Caspase 8, Caspase 9, ALG2 (Alpha-1,3/1,6-mannosyltransferase), REQ (Requiem), FADD (Fas (TNFRSF6)-associated via death domain), FAIM (Fas apoptotic inhibitory molecule), NEU2 (Sialidase 2), NEU1 (Sialidases 1), NEU3 (Sialidases 3), GMD (GDP-fucose 4,6-dehydratase), GFT (GDP-fucose transporter), CFL1 (Cofilin), ATR (Ataxia telangiectasia and Rad3 related), ENO1 (Enolase 1) and PDHK (Pyruvate dehydrogenase kinase).

In an embodiment of the present invention, the intronic RNA sequence for target gene expression regulation may be at least one sequence selected from the group consisting of shRNA (short hairpin RNA), miRNA (micro RNA), stRNA (small temporal RNA), siRNA (small interfering RNA), piRNA (piwi-interacting RNA), snoRNA (small nucleolar RNA), snRNA (small nuclear RNA), exRNA (extracellular RNA), scaRNA (small cajal body RNA), lncRNA (long noncoding RNA), smRNA (small modulatory dsRNA), and snRNA (small noncoding RNA).

In an embodiment of the present invention, the shRNA sequence for target gene expression regulation may be at least one selected from the group consisting of intronic FUT8 shRNA represented by SEQ ID NO: 24, intronic HDAC5 (histone deacetylase 5) shRNA represented by any one of SEQ ID NOS: 25 to 27, intronic LDHA (lactate dehydrogenase A) shRNA represented by any one of SEQ ID NOS: 28 to 30, and intronic DHFR (dihydrofolate reductase) shRNA represented by any one of SEQ ID NOS: 31 to 33.

In an embodiment of the present invention, the intronic miRNA sequence for target gene regulation may be miR483 represented by any one of SEQ ID NOS: 34 to 36.

In an embodiment of the present invention, the splicing donor sequence may be at least one selected from among SEQ ID NOS: 12 to 15, the branch sequence may be at least one selected from among SEQ ID NOS: 16 to 18, and the splicing acceptor sequence may be at least one selected from among SEQ ID NOS: 19 to 22.

In an embodiment of the present invention, the expression cassette for production of a target protein may have at least one effect selected from the group consisting of increased expression of a target protein, inhibition of lactate production, regulation of histone protein deacetylation, regulation of glucose metabolism, regulation of cell growth, regulation of cell proliferation, increased functionality of a target protein, and decreased fucose content of a target protein, through intron splicing or endogenous gene expression regulation.

In addition, the present invention provides a vector including the expression cassette for production of a target protein.

In addition, the present invention provides a transformant, which is transformed with the vector including the expression cassette for production of a target protein.

In an embodiment of the present invention, the transformant may be a eukaryotic cell.

In addition, the present invention provides a method of manufacturing a target protein including culturing a transformant including the expression cassette for production of a target protein.

Advantageous Effects

According to the present invention, a target protein expression cassette can simultaneously express an intron sequence and a target protein through a single transfection, and has the effect of inducing high expression and high functionality of a target protein by regulating the expression of an endogenous gene. In addition, an expression vector according to the present invention is configured such that a target protein and an intron sequence are transcriptionally linked by a single promoter, and thus, even when a cell line is selected by checking only the expression of the target protein, it is possible to effectively select a cell line in which transcription of the intron sequence is efficient.

MODE FOR INVENTION

Figure 1:
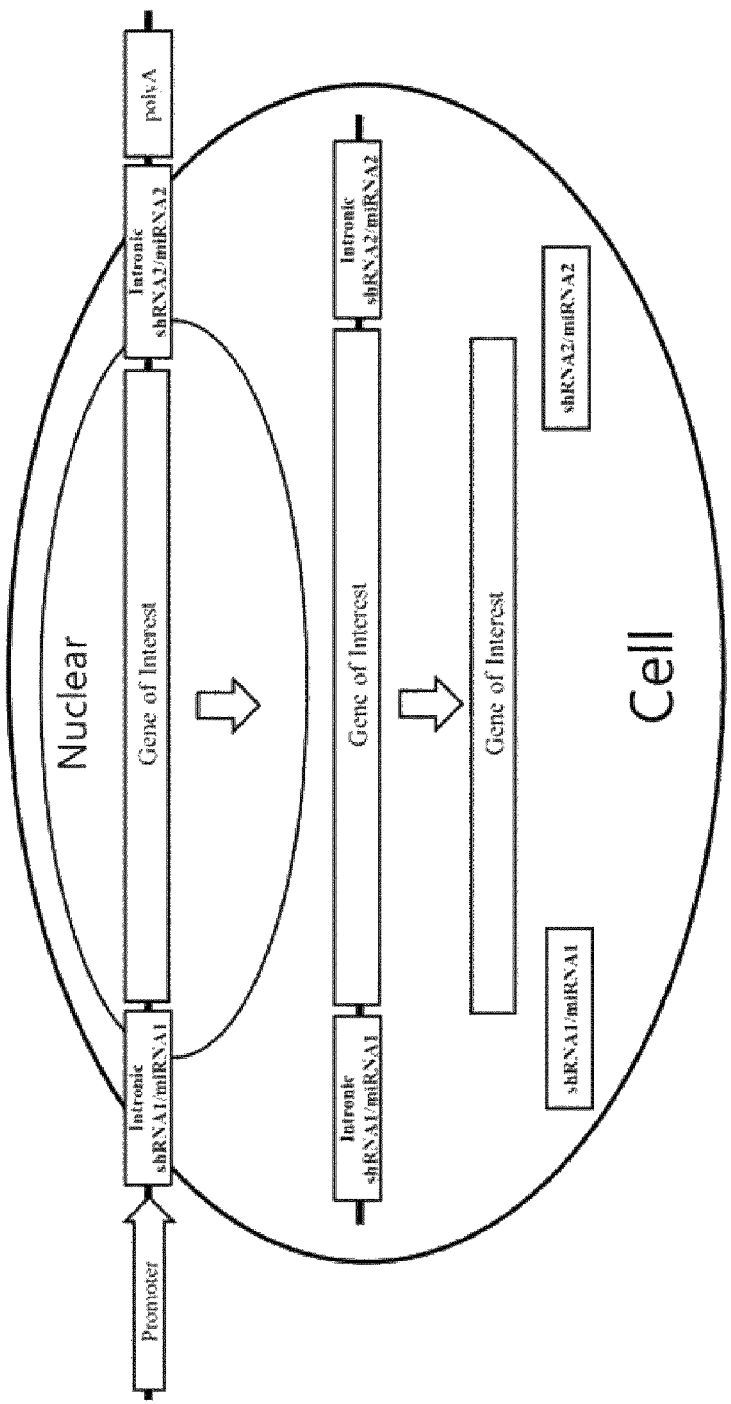
FIG. 1 schematically shows the structure of an expression cassette of a recombinant protein including intronic shRNA/miRNA, based on the principle of the present invention whereby shRNA/miRNA and a recombinant protein are made through an intron-splicing process after transfection into cells.

The present invention pertains to an expression cassette for production of a high-expression and high-functionality target protein including a promoter and to the use thereof.

According to the present invention, an expression vector may simultaneously express an intron sequence and a recombinant protein of interest through a single transfection, and has the effect of inducing high expression and high functionality of a recombinant protein by regulating the expression of an endogenous gene. Moreover, the expression vector according to the present invention is configured such that a recombinant protein and a shRNA sequence are transcriptionally linked by a single promoter, and thus, even when a cell line is selected by checking only the expression of the recombinant protein, it is possible to effectively select a cell line in which transcription of shRNA is efficient.

Furthermore, the expression vector according to the present invention has the effect of regulating multiple endogenous genes through a single transfection.

When an antibody is produced as a target protein using the expression vector according to the present invention, an intronized shRNA sequence may suppress the expression of a glycosylation-related gene (e.g. FUT8) to thus produce an antibody in which fucose glycosylation of the antibody is inhibited. Alternatively, the intronized shRNA sequence may suppress the expression of an apoptosis-related gene to thus increase the production level of the antibody.

In order to more easily understand the present invention, the terms used herein are defined below.

"Target protein" refers to a protein to be produced.

"Intronic RNA sequence" refers to the RNA sequence of a portion that is removed as an intron during the transcription of DNA into mRNA. It includes a splicing donor, a splicing acceptor and a branch. Typically, a splicing donor has a specific sequence, such as AG_GTRAGT (R: A or G), a splicing acceptor has a specific sequence, such as YYYYYYYYYYNCAG_G (Y: C or T; N: A, G, C or T), and a branch has a specific sequence, such as YTRAC. In addition to these sequences, all sequences that may be spliced are included. The intronic RNA sequence may or may not be functional in itself.

"Poly A sequence" refers to a continuous sequence of adenylic acid located at the 3' mRNA end.

The "splicing donor" and the "splicing acceptor" are sequences that allow a splicing process to occur, the splicing donor being located at position 5' of the intron and the splicing acceptor being located at position 3' of the intron.

The "branch" is the portion that includes nucleotide adenine and is involved in the formation of a lariat structure during the splicing process.

"Expression cassette" refers to a unit cassette that includes a promoter and a polynucleotide sequence encoding a target protein and is capable of expressing the target protein in order to produce the target protein. The expression cassette may include therein various factors that may be helpful for efficient production of the target protein. More specifically, the expression cassette may include a promoter, a polynucleotide coding for the target protein, and a poly A sequence.

"Antibody" refers to an immunoglobulin molecule composed of four polypeptide chains, in which two heavy chains and two light chains are connected to each other by disulfide bonds. Other naturally occurring antibodies having altered structures, such as camelid antibodies, are also included in this definition. Each heavy chain is composed of a heavy-chain variable region and a heavy-chain constant region. The heavy-chain constant region is composed of three domains (CH1, CH2 and CH3). Each light chain is composed of a light-chain variable region and a light-chain constant region. The light-chain constant region is composed of one domain (CL). The heavy-chain variable region and the light-chain variable region may be further subdivided into more conserved regions called framework regions (FR) and hypervariable regions called complementarity-determining regions (CDR). Each of the heavy-chain variable region and the light-chain variable region is composed of 3 CDRs and 4 FRs, which are arranged in the following order from the amino terminus to the carboxyl terminus: FR1, CDR1, FR2, CDR2, FR3, CDR3, and FR4.

"Expression regulation" means to regulate the expression level of a specific gene, and "regulation" includes the concept of both increasing and decreasing the same.

The "shRNA" is a hairpin-structure RNA including a short interference RNA (siRNA) sequence, and is processed into short interference RNA by an RNase enzyme called a dicer in a cell.

Various aspects of the present invention are described in further detail herein.

The present invention pertains to an expression cassette for production of a target protein, which is a target protein expression cassette including a promoter, a polynucleotide coding for the target protein, a polynucleotide sequence encoding an intronic RNA sequence and a poly A sequence, the intronic RNA sequence including a splicing donor, a branch and a splicing acceptor.

FIG. 1 of the present invention schematically shows the structure of the expression cassette of a recombinant protein including intronic shRNA/miRNA. This is based on the principle of the present invention whereby shRNA/miRNA and a recombinant protein are made through an intron-splicing process after transfection into cells.

The present invention pertains to a method capable of improving the productivity and functionality of a target protein through splicing after the intronic RNA sequence and the target protein sequence are transcribed into one mRNA using a single promoter.

The promoter may be used without limitation, so long as it is a promoter able to operate the expression cassette of the present invention, and is preferably a polII-type promoter. More preferable is a polII-type promoter selected from the group consisting of CMV (cytomegalovirus), EF1α (elongation factor 1 alpha), CEF (CMV early enhancer/EF1α promoter and intron), CBA (chickenbeta-actin), CAG (CMV early enhancer/chicken beta-actin promoter & intron), CBh (CMV early enhancer/chicken beta-actin promoter), GAPDH (Glyceraldehyde 3-phosphate dehydrogenase), SV40 (Simian virus 40), UBC (ubiquitin C), PGK (phosphoglycerate kinase), LTR (long terminal repeats), GUSB (β glucuronidase), UCOE (ubiquitous chromatin opening element), WAS proximal promoter, CD4 mini-promoter/enhancer, CD2 locus control region, CD4 minimal promoter/proximal enhancer/silencer, CD4 mini-promoter/enhancer, GATA-1 enhancer HS2 within the LTR, Ankyrin-1/α-spectrin promoters/HS-40, GATA-1, ARE/intron 8 enhancers, Ankyrin-1 promoter/β-globin HS-40 enhancer, GATA-1 enhancer HS1 to HS2/retroviral LTR, MCH HLA-DR promoter, Fascin promoter, Dectin-2 gene promoter, 5' untranslated region from the DC-STAMP, Heavy chain intronic enhancer (Eµ)/matrix attachment regions, CD19 promoter, Hybrid immunoglobulin promoter (Igk promoter, intronic Enhancer/3' enhancer from Ig genes), CD68L promoter/first intron, Glycoprotein Ib α promoter, hAAT (α1-antitrypsin), ApoE (Apolipoprotein E), ApoE/hAAT (Apolipoprotein E enhancer/alpha1-antitrypsin) promoter, HAAT promoter/Apo E locus control region, Albumin promoter, HAAT promoter/four copies of the Apo E enhancer, HAAT promoter/Apo E locus control region, hAAT promoter/four copies of the Apo E enhancer, Thyroid hormone-binding globulin promoter/al-microglobulin/bikunin enhancer, DC172 promoter (al-antitrypsin promoter/al-microglobulin enhancer), LCAT, kLSP-IVS, ApoE/hAAT/liver-fatty acid-binding protein promoters, RU486-responsive promoter, Creatine kinase promoter, C5-12 (Synthetic muscle-specific promoter), MHCK7 (Hybrid enhancer/promoter regions of α-myosin and creatine kinase), Cardiac troponin-I proximal promoter, E-selectin/KDR promoters, Prepro-endothelin-1 promoter, KDR promoter/hipoxia-responsive element, Flt-1 (fms-like tyrosine kinase-1) promoter, ICAM-2 (intercellular adhesion molecule2) promoter, Synthetic endothelial promoter, Endothelin-1 gene promoter, Amylase promoter, Insulin and human pdx-1 promoters, TRE-regulated insulina promoter, Enolase promoter, TRE-regulated synapsin promoter, Synapsin 1 promoter, PDGF (platelet-derived growth factor), PDGF-β promoter/CMV enhancer, tubulin-α,$Ca^{2+}$/calmodulin-PK2 promoters/CMV enhancer, Phosphate-activated glutaminase/vesicular glutamate transporter-1 promoters, Glutamic acid decarboxylase-67 promoter, Tyrosine hydroxylase promoter, Neurofilament heavy gene promoter, Human red opsin promoter, Keratin-18 promoter, Keratin-14 promoter, Keratin-5 promoter, CD40L promoter, β-Globin promoter/LCR, β-Globin and -globin promoters/HS-40, GATA-1, ARE/intron 8 enhancers, β-Globin, LCR HS4, HS3, HS2/truncated β-globin intron 2, β-Globin promoter/LCR/cHS4, HSFE/LCR/β-globin promoter, Integrinα Iib promoter, Dystrophin promoter/regulatory sequences, Endoglin promoter, RPE65 promoter, TBG (thyroxine binding globulin), Desmin, MCK (muscle creatine kinase), NSE (neuronal-specific endolase), MeCP2 (methyl-CpG binding protein 2), CaMKII (calcium/calmodulin dependent protein kinase II), mGluR2, NFL, NFH, nB2, PPE, Enk, EAAT2, GFAP (glial fibrillary acidic protein), MBP (Myelin basic protein), Myosin heavy-chain, Myosin light-chain, MND (a synthetic promoter that contains the U3 region of a modified MoMuLV LTR with myeloproliferative sarcoma virus enhancer), CYP2E1 (Cytochrome P450 2E1), MeCP2 (methyl-CpG binding protein 2) CMV (cytomegalovirus), EF1α (elongation factor 1 alpha), CEF (CMV early enhancer/EF1α promoter and intron), CBA (chickenbeta-actin), CAG (CMV early enhancer/chicken beta-actin promoter & intron), CBh (CMV early enhancer/chicken beta-actin promoter), GAPDH (Glyceraldehyde 3-phosphate dehydrogenase), SV40 (Simian virus 40), UBC (ubiquitin C), PGK (phosphoglycerate kinase), LTR (long terminal repeats), GUSB (β glucuronidase), UCOE (ubiquitous chromatin opening element), WAS proximal promoter, CD4 mini-promoter/enhancer, CD2 locus control region, CD4 minimal promoter/proximal enhancer/silencer, CD4 mini-promoter/enhancer, GATA-1 enhancer HS2 within the LTR, Ankyrin-1/α-spectrin promoters/HS-40, GATA-1, ARE/intron 8 enhancers, Ankyrin-1 promoter/β-globin HS-40 enhancer, GATA-1 enhancer HS1 to HS2/retroviral LTR, MCH HLA-DR promoter, Fascin promoter, Dectin-2 gene promoter, 5' untranslated region from the DC-STAMP, Heavy chain intronic enhancer (Eμ)/matrix attachment regions, CD19 promoter, Hybrid immunoglobulin promoter (Igk promoter, intronic Enhancer/3' enhancer from Ig genes), CD68L promoter/first intron, Glycoprotein Ib α promoter, hAAT (α1-antitrypsin), ApoE (Apolipoprotein E), ApoE/hAAT (Apolipoprotein E enhancer/alpha1-antitrypsin) promoter, HAAT promoter/Apo E locus control region, Albumin promoter, HAAT promoter/four copies of the Apo E enhancer, HAAT promoter/Apo E locus control region, hAAT promoter/four copies of the Apo E enhancer, Thyroid hormone-binding globulin promoter/al-microglobulin/bikunin enhancer, DC172 promoter (al-antitrypsin promoter/al-microglobulin enhancer), LCAT, kLSP-IVS, ApoE/hAAT/liver-fatty acid-binding protein promoters, RU486-responsive promoter, Creatine kinase promoter, C5-12 (Synthetic muscle-specific promoter), MHCK7 (Hybrid enhancer/promoter regions of α-myosin and creatine kinase), Cardiac troponin-I proximal promoter, E-selectin/KDR promoters, Prepro-endothelin-1 promoter, KDR promoter/hipoxia-responsive element, Flt-1 (fins-like tyrosine kinase-1) promoter, ICAM-2 (intercellular adhesion molecule2) promoter, Synthetic endothelial promoter, Endothelin-1 gene promoter, Amylase promoter, Insulin and human pdx-1 promoters, TRE-regulated insulina promoter, Enolase promoter, TRE-regulated synapsin promoter, Synapsin 1 promoter, PDGF (platelet-derived growth factor), PDGF-β promoter/CMV enhancer, tubulin-α,$Ca^{2+}$/calmodulin-PK2 promoters/CMV enhancer, Phosphate-activated glutaminase/vesicular glutamate transporter-1 promoters, Glutamic acid decarboxylase-67 promoter, Tyrosine hydroxylase promoter, Neurofilament heavy gene promoter, Human red opsin promoter, Keratin-18 promoter, Keratin-14 promoter, Keratin-5 promoter, CD40L promoter, β-Globin promoter/LCR, β-Globin and -globin promoters/HS-40, GATA-1, ARE/intron 8 enhancers, 13-Globin, LCR HS4, HS3, HS2/truncated β-globin intron 2, β-Globin promoter/LCR/cHS4, HSFE/LCR/β-globin promoter, Integrinα Iib promoter, Dystrophin promoter/regulatory sequences, Endoglin promoter, RPE65 promoter, TBG (thyroxine binding globulin), Desmin, MCK (muscle creatine kinase), NSE (neuronal-specific endolase), MeCP2 (methyl-CpG binding protein 2), CaMKII (calcium/calmodulin dependent protein kinase II), mGluR2, NFL, NFH, nB2, PPE, Enk, EAAT2, GFAP (glial fibrillary acidic protein), MBP (Myelin basic protein), Myosin heavy-chain, Myosin light-chain, MND (a synthetic promoter that contains the U3 region of a modified MoMuLV LTR with myeloproliferative sarcoma virus enhancer), CYP2E1 (Cytochrome P450 2E1) and MeCP2 (methyl-CpG binding protein 2) promoter. Most preferably, the promoter is a CMV (cytomegalovirus) promoter.

For the effective transcription of short fragment DNA such as shRNA, it is necessary to use a polIII-type promoter. However, these polIII-type promoters are difficult to induce the high expression of a target protein, so expression cassettes having respective promoters are required in order to express shRNA and target protein. Therefore, it is difficult to manufacture at once a cell line that regulates the expression of a target protein and the expression of an endogenous gene due to problems with the size of the expression cassettes, transfection and selection processes. In order to overcome these problems, a polII-type CMV promoter, which is a strong promoter, is used, and an intron sequence is arranged at both ends of the sequence so that the DNA sequence of shRNA is able to form a shRNA structure capable of post-transcriptional gene regulation. Thus, shRNAs are produced through splicing during the transcription process, and the shRNAs thus produced regulate the expression of specific endogenous genes. Simultaneously, the target protein that is transcribed and expressed with the same CMV promoter exhibits increased production level and functionality due to the regulation of the expression of the endogenous gene.

The target protein may be of any type, but is preferably an antibody or a fragment thereof.

In an embodiment of the present invention, the antibody or the fragment thereof may have specificity to any one target antigen selected from the group consisting of CD19, CD20, CD22, CD33, CD52, Her2/neu, EGFR, EpCAM, MUC1, GD3, CEA, CA125, HLA-DR, TNF-α, VEGF, Integrinα4β7, IL-12, IL-23, Anti-CD20 Mab, IL-6R, VEGF receptor kinase inhibitor, complement factor C5, IL-1 beta, RANK ligand, VEGFR2 (KDR), IL-6, GD20, IL-5, PDGF-Rα, CTLA-4, CD3, IL-17A, PD-L1, PD-1, BAFF, BLyS, Dabigatran, SLAMF7 (cD319), Anti-IL-4, IL-13 Mab,

*Bacillus anthracis* anthrax, CD25, *Clostridium difficile* toxin B, PCSK9, hemagglutinin (HA) of influenza virus, F protein of RSV (respiratory syncytial virus), G protein of RSV, IgE (immunoglobulin E), and G protein of Rabies virus.

In an embodiment of the present invention, a polynucleotide sequence encoding at least one intronic RNA sequence may be present on a single target protein expression cassette. The expression vector of the present invention includes sequence information of at least one shRNA/miRNA targeting endogenous genes of interest in animal cells, and includes an intron sequence that allows at least one shRNA/miRNA to be generated.

In an embodiment of the present invention, the expression cassette may include a polynucleotide sequence encoding at least one intronic RNA sequence selected from the group consisting of: a) a polynucleotide sequence encoding at least one intronic RNA sequence located between a promoter and a polynucleotide coding for the target protein, b) a polynucleotide sequence encoding at least one intronic RNA sequence located between a polynucleotide coding for the target protein and a poly A, and c) a polynucleotide sequence encoding at least one intronic RNA sequence located between a promoter and a polynucleotide coding for the target protein and a polynucleotide sequence encoding at least one intronic RNA sequence located between a polynucleotide coding for the target protein and a poly A.

Figure 2:
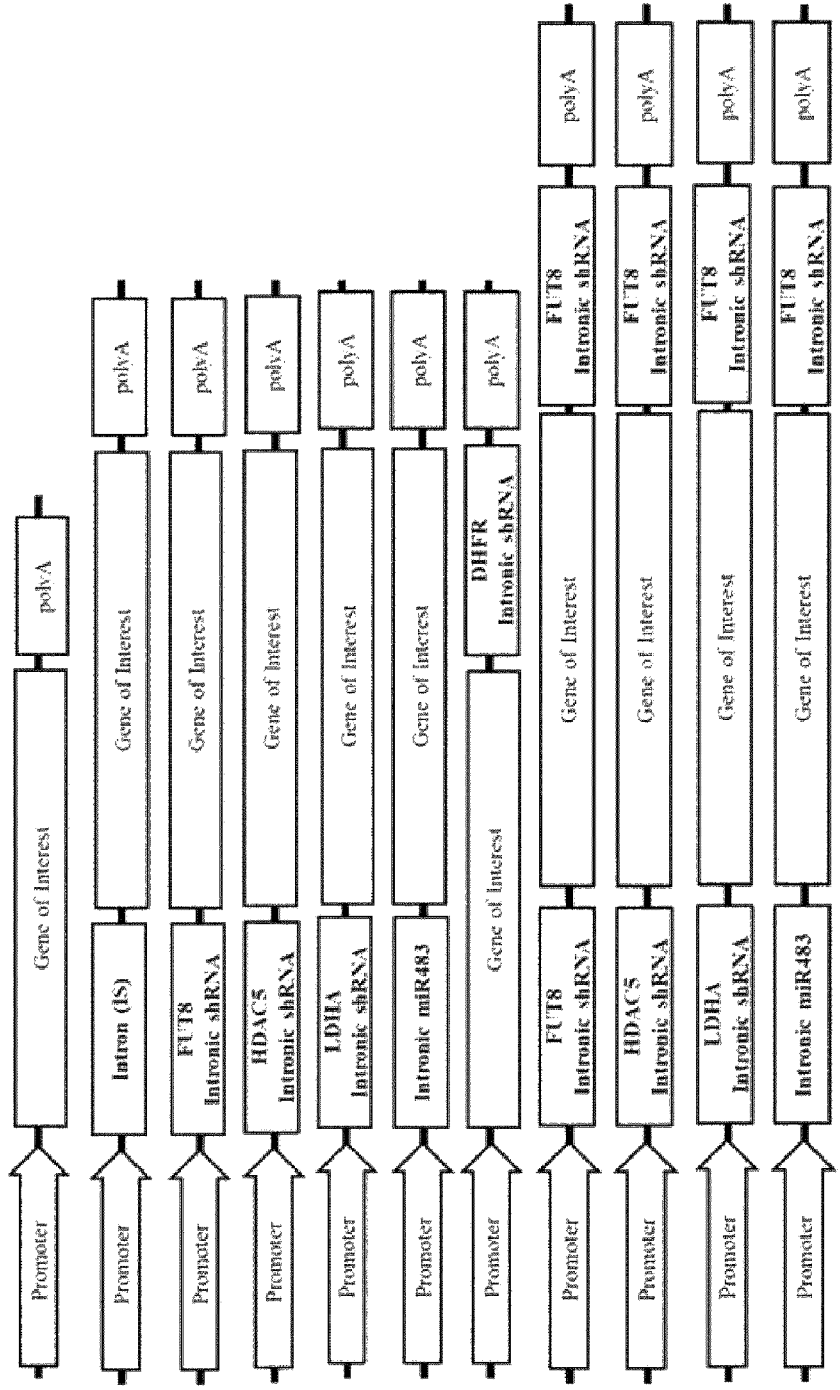
FIG. 2 schematically shows an intron-free recombinant protein (antibody) expression vector (control), an antibody expression vector including an intron sequence (IS) having no endogenous gene regulation function, and an antibody expression vector including intronic shRNA/miRNA for endogenous gene regulation.

FIG. 2 of the present invention schematically shows an intron-free recombinant protein (antibody) expression vector (control), an antibody expression vector including an intron sequence (IS) having no endogenous gene regulation function, and an antibody expression vector including intronic shRNA/miRNA for endogenous gene regulation, from which it can be seen that at least one intronic RNA sequence may be included.

In an embodiment of the present invention, the intronic RNA sequence may further include an RNA sequence for target gene expression regulation.

In an embodiment of the present invention, the target gene may be at least one selected from the group consisting of FUT8 (Alpha-1,6-fucosyltransferase), HDAC5 (Histone Deacetylase 5), LDHA (Lactate dehydrogenase A), CXCR4 (C—X—C chemokine receptor type 4), DHFR (Dihydrofolate reductase), PDK4 (Pyruvate dehydrogenase lipoamide kinase isozyme 4), MAPK3 (Mitogen-activated protein kinase 3), KANK4 (KN Motif And Ankyrin Repeat Domains 4), PDI (Protein disulfide isomerase), CNX (Calnexin), CRT (Calreticulin), eIF2alpha (Non-phosphorylatable version of the eukaryotic translation initiation factor 2 alpha), ZFP-TF (Artificial zinc finger protein transcription factor), ATF4 (Activating transcription factor 4), GADD34 (Growth arrest and DNA damage inducible protein 34), mTOR (Mammalian target of rapamycin), BIP (Heat shock 70 kDa protein 5), ATF6C (Activating transcription factor 6C), XBP1 (X-box binding protein 1), BCL2 (B-cell lymphoma 2), BCLxL (BCL2-like 1), Mutated form of BCL-xL (Asp29Asn variant), XIAP (X-linked inhibitor of apoptosis), a mutant form of XIAREAX197), AVEN (Apoptosis, caspase inhibitor), C-MYC (Myelocytomatosis oncogene), FAIM (Fas apoptotic inhibitory molecule), 30Kc6 (Apoptosis-inhibiting 30K protein), TERT (Telomerase reverse transcriptase), E1B-19K (Control protein E1B 19K), MDM2 (Murine double-mutant 2), E2F1 (E2F transcription factor 1), HSP27 (Heat shock proteins 27), HSP70 (Heat shock proteins 70), MCL1 (Myeliod cell leukemia 1), AKT1 (RAC-alpha serine/threonineprotein kinase), Beclin-1, ST6GAL (Alpha 2,6 sialyltransferase), GnT-IV (Alpha-1,3-D-mannoside beta 1,4 Nacetylglucosaminyltransferase), GnT-V (alpha 1,6 Dmannoside beta-1,6 Nacetylglucosaminyltransferase), ST3GAL (Alpha 2,3 sialyltransferase), GalT (beta 1,4 galactosyltransferase), CMP-SAT (CMP-sialic acid transporter), CMP-SAS (CMP-sialic acid synthetase), GNE (Mutant uridine diphosphate-N-acetyl glucosamine 2-epimerase), GnT-III (Beta 1,4 Nacetylglucosaminyltransferase ManII (Golgi alphamannosidase II), C2GnT (Beta 1,6 Nacetylglucosaminyltransferase), RMD (GDP-6-deoxy-d-lyxo-4-hexulose reductase), VHb (*Vitreoscilla* hemoglobin), CPS Karbamoyl phosphate synthetase I), OTC (Ornithine transcarbamoylase), PC (Pyruvate carboxylase), GLUT5 (Glucose transporter protein 5), MDH2 (Malate dehydrogenase II), TAUT (Taurine transporter), ALT1 (Alanine aminotransferase 1), XBP1 (X-box binding protein 1), XBP1s (Spliced form of XBP-1), SLY1 (Suppressor of loss of YPT1 protein 1), MUNC18C (syntaxin binding protein 3), CERT (Ceramide transfer protein), Mutant form of CERT (S132A), SNAP-23 (Synaptosome-associated protein of 23 kDa), VAMP8 (Vesicle-associated membrane protein 8), SRP14 (Human signaling receptor protein 14), p21CIP1 (Cyclin-dependent kinase Inhibitor 1A), C/EBP-alpha (CCAAT/enhancer-binding protein alpha), p27KIP1 (Cyclin-dependent kinase inhibitor 1B), CDKL3 (Cyclin-dependent kinase like 3), COX15 (Cytochrome c oxidase subunit), VCP (Valosin-containing protein), BAX (BCL2-associated X protein), BAK (BCL2-antagonist/killer), GS (Glutamine synthetase), MGAT1 (N-acetylglucosaminyltransferase 1), SLC35C1 (GDP-fucose transporter), SLC35A1 (CMPsialic acid transporter), B4GALT1 (Beta 1,4 galactosyltransferase 1), B3GNT2 (Beta 1,3 Nacetylglucosaminyltransferase 2), PAM (Peptidylglycine alphaamidating monooxygenase), Caspase 3, Caspase 7, Caspase 8, Caspase 9, ALG2 (Alpha-1,3/1,6-mannosyltransferase), REQ (Requiem), FADD (Fas(TN-FRSF6)-associated via death domain), FAIM (Fas apoptotic inhibitory molecule), NEU2 (Sialidase 2), NEU1 (Sialidases 1), NEU3 (Sialidases 3), GMD (GDP-fucose 4,6-dehydratase), GFT (GDP-fucose transporter), CFL1 (Cofilin), ATR (Ataxia telangiectasia and Rad3 related), ENO1 (Enolase 1) and PDHK (Pyruvate dehydrogenase kinase). More preferable is at least one selected from the group consisting of FUT8 (Alpha-1,6-fucosyltransferase), HDAC5 (Histone Deacetylase 5), LDHA (Lactate dehydrogenase A), DHFR (Dihydrofolate reductase), PDK4 (Pyruvate dehydrogenase lipoamide kinase isozyme 4), CXCR4 (C—X—C chemokine receptor type 4), MAPK3 (Mitogen-activated protein kinase 3) and KANK4 (KN Motif and Ankyrin Repeat Domains 4).

In an exemplary embodiment of the present invention, as an endogenous gene for expression regulation, alpha 1,6-fucosyltransferase (FUT8), which plays a role in glycosylation of fucose that is involved in antibody-dependent cytotoxicity, was selected and tested, and an antibody having almost no fucose due to effective inhibition of the expression of FUT8 was produced.

In an embodiment of the present invention, the RNA sequence for target gene expression regulation may be at least one sequence selected from the group consisting of shRNA (short hairpin RNA), miRNA (micro RNA), stRNA (small temporal RNA), siRNA (small interfering RNA), piRNA (piwi-interacting RNA), snoRNA (small nucleolar RNA), snRNA (small nuclear RNA), exRNA (extracellular RNA), scaRNA (small Cajal body RNA), lncRNA (long noncoding RNA), smRNA (small modulatory dsRNA), and snRNA (small noncoding RNA). Most preferable is at least one sequence selected from the group consisting of shRNA (short hairpin RNA), miRNA (micro RNA), stRNA (small temporal RNA), and siRNA (small interfering RNA).

In an embodiment of the present invention, the shRNA sequence for target gene expression regulation may be at least one sequence selected from the group consisting of intronic FUT8 shRNA represented by SEQ ID NO: 24, intronic HDAC5 (histone deacetylase 5) shRNA represented by any one of SEQ ID NOS: 25 to 27, intronic LDHA (lactate dehydrogenase A) shRNA represented by any one of SEQ ID NOS: 28 to 30, and intronic DHFR (dihydrofolate reductase) shRNA represented by any one of SEQ ID NOS: 31 to 33.

Figure 3:
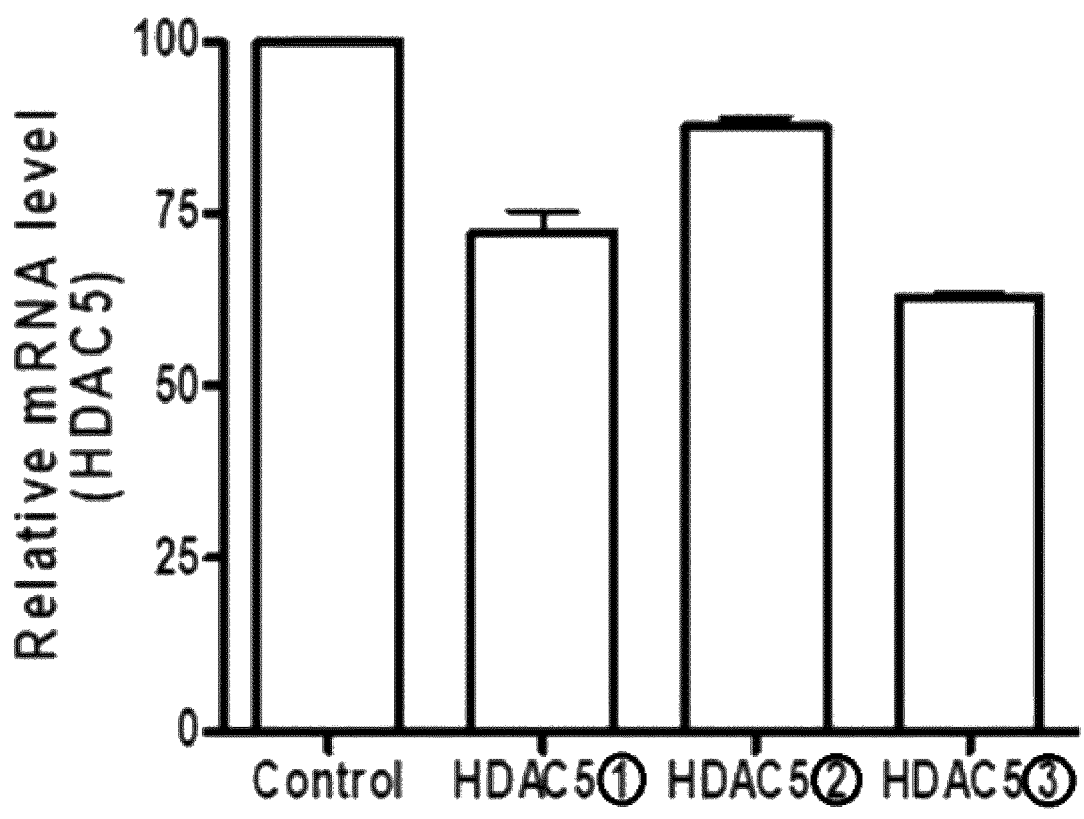
FIG. 3 is a graph showing the results of measurement of the amount of mRNA of HDAC5 regulated by shRNA using a quantitative RT-PCR process after transfection with an antibody expression vector including intronic shRNA for HDAC5 regulation.

Here, shRNA that inhibits the gene expression of HDCA5 is preferably any one selected from the group consisting of SEQ ID NOS: 25 to 27, and is most preferably intronic HDAC5 shRNA represented by SEQ ID NO: 27. In an embodiment of the present invention, based on experimental results on the effect of inhibition of the expression of HDAC5 with intronic HDAC5 shRNAs represented by SEQ ID NOS: 25 to 27, intronic HDAC5 shRNA represented by SEQ ID NO: 27 inhibited the expression of HDAC5 most effectively (FIG. 3).

Figure 4:
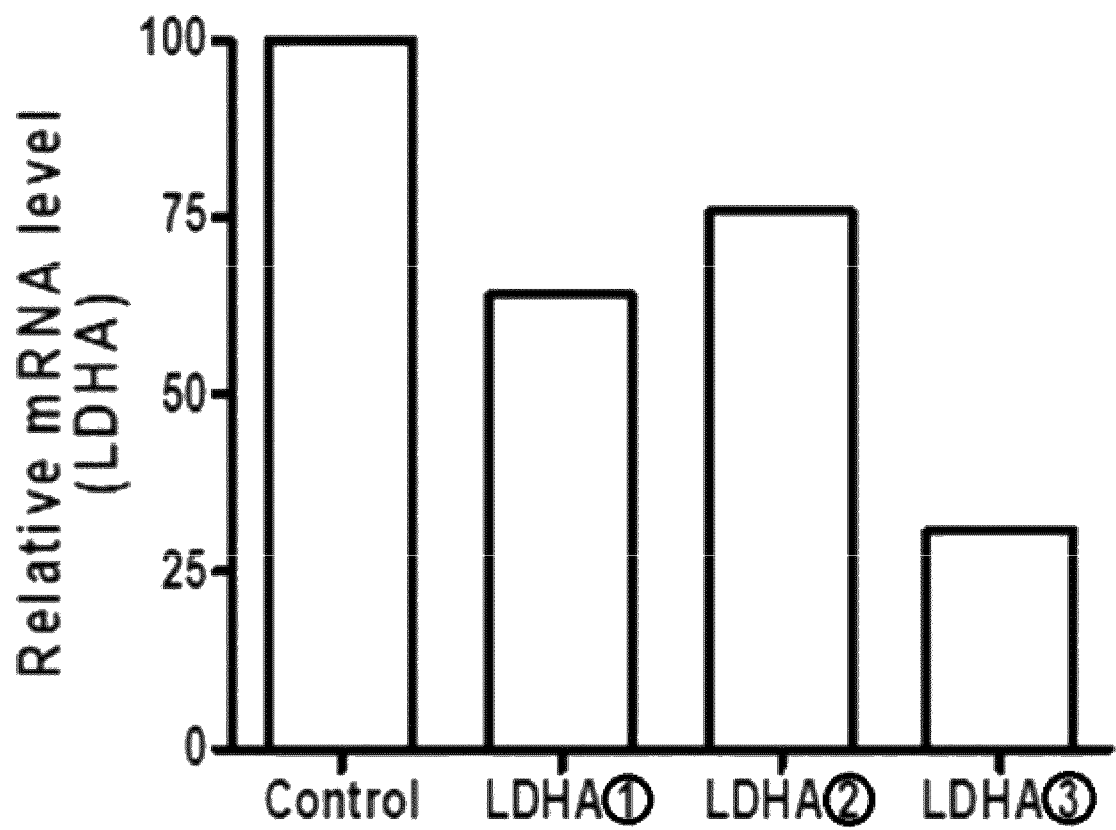
FIG. 4 is a graph showing the results of measurement of the amount of mRNA of LDHA regulated by shRNA using a quantitative RT-PCR process after transfection with an antibody expression vector including intronic shRNA for LDHA regulation.

Also, shRNA that inhibits the gene expression of LDHA is preferably any one selected from the group consisting of SEQ ID NOS: 28 to 30, and is most preferably intronic LDHA shRNA represented by SEQ ID NO: 30. In an embodiment of the present invention, based on experimental results on the effect of inhibition of the expression of LDHA with intronic LDHA shRNAs represented by SEQ ID NOS: 28 to 30, intronic LDHA shRNA represented by SEQ ID NO: 30 inhibited the expression of LDHA most effectively (FIG. 4).

Figure 5:
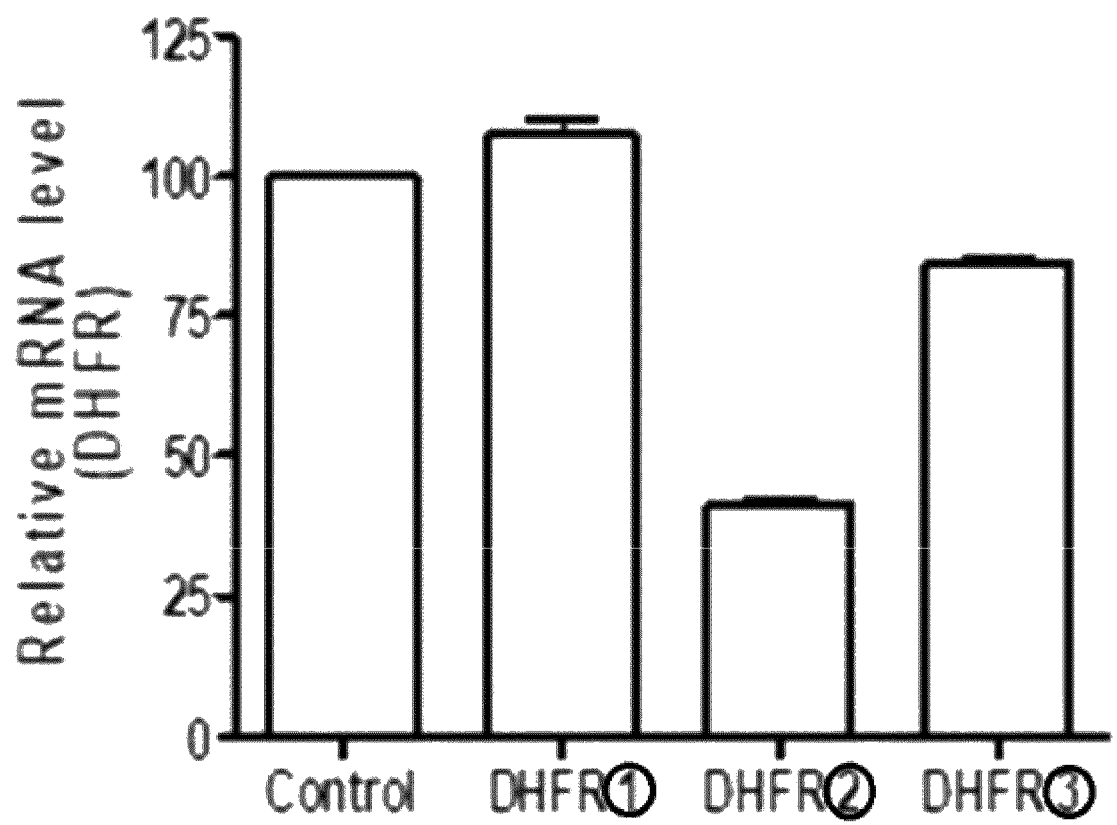
FIG. 5 is a graph showing the results of measurement of the amount of mRNA of DHFR regulated by shRNA using a quantitative RT-PCR process after transfection with an antibody expression vector including intronic shRNA for DHFR regulation.

Also, shRNA that inhibits the gene expression of DHFR is preferably any one selected from the group consisting of SEQ ID NOS: 31 to 33, and is most preferably intronic DHFR shRNA represented by SEQ ID NO: 32. In an embodiment of the present invention, based on experimental results on the effect of inhibition of the expression of DHFR with intronic DHFR shRNAs represented by SEQ ID NOS: 31 to 33, intronic DHFR shRNA represented by SEQ ID NO: 32 inhibited the expression of DHFR most effectively (FIG. 5).

Figure 6:
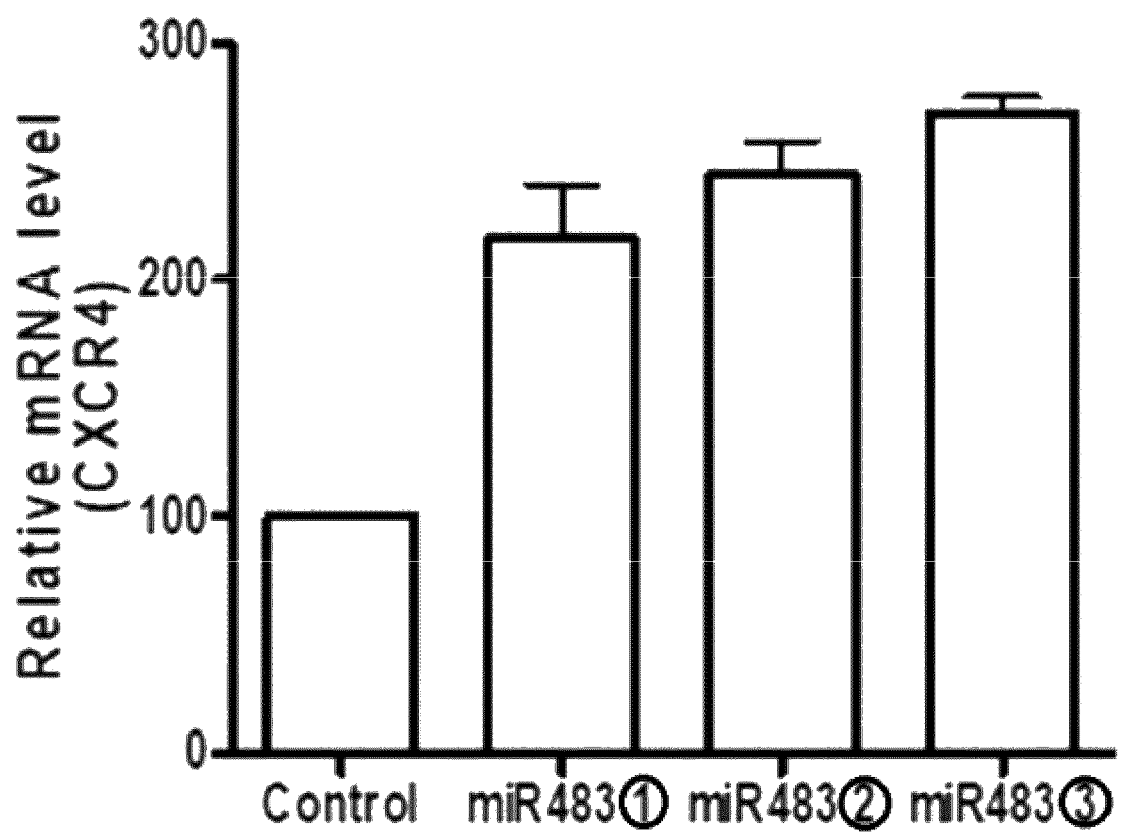
FIG. 6 is a graph showing the results of measurement of the amount of mRNA of CXCR4 regulated by miR483 using a quantitative RT-PCR process after transfection with an antibody expression vector including intronic miR483.
Figure 7:
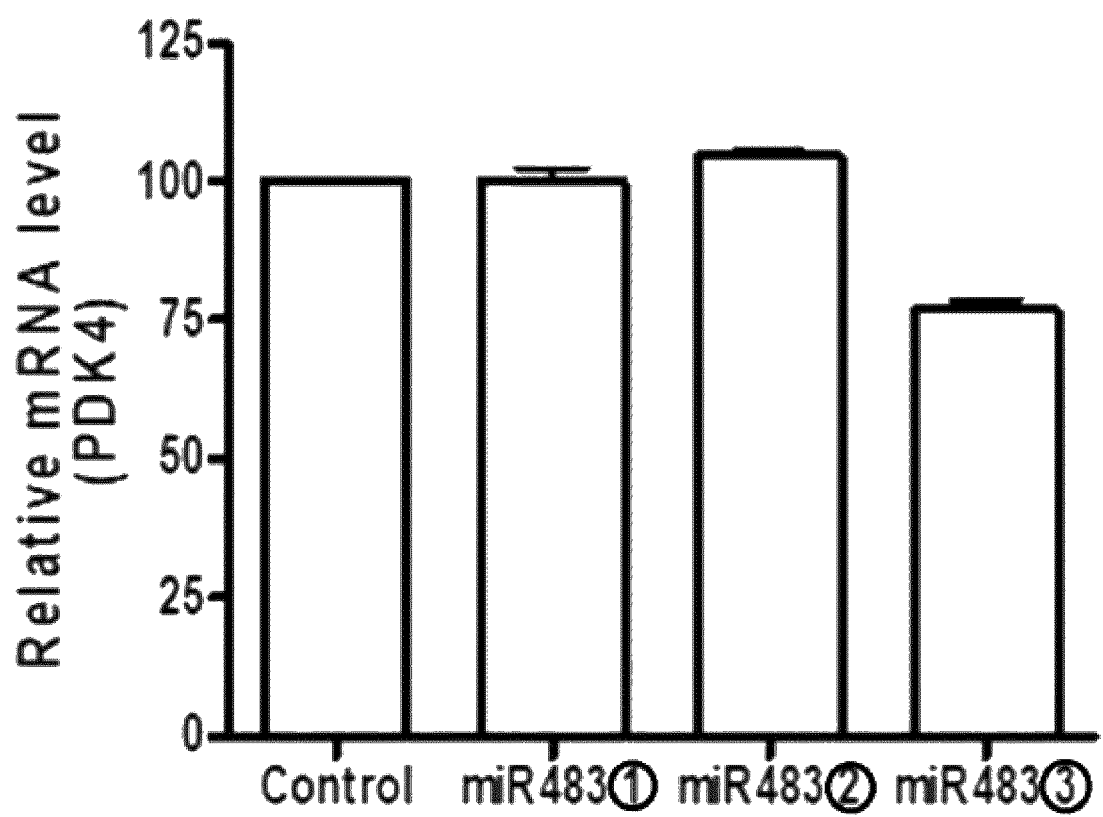
FIG. 7 is a graph showing the results of measurement of the amount of mRNA of PDK4 regulated by miR483 using a quantitative RT-PCR process after transfection with an antibody expression vector including intronic miR483.

In an embodiment of the present invention, the miRNA sequence for target gene regulation may be intronic miR483 represented by any one of SEQ ID NOS: 34 to 36. In an embodiment of the present invention, in order to maximize the inhibition of PDK4 target expression and the increase in CXCR4 target expression when manufacturing an expression cassette including intronic miR483, an experiment was conducted to determine the optimal branch sequence and splicing acceptor combination. Individual intronic RNA sequences represented by SEQ ID NOS: 34 to 36 were constructed using different branch sequences and splicing acceptors. Thereafter, based on the results of measurement of the effects of inhibiting the expression of PDK4 and increasing the expression of CXCR4, the intronic miR483 sequence represented by SEQ ID NO: 36 was found to be the most effective (FIGS. 6 and 7).

In an embodiment of the present invention, the splicing donor sequence may be at least one selected from among SEQ ID NOS: 12 to 15, the branch sequence may be at least one selected from among SEQ ID NOS: 16 to 18, and the splicing acceptor sequence may be at least one selected from among SEQ ID NOS: 19 to 22.

In an embodiment of the present invention, the expression cassette for production of a target protein may have at least one effect selected from the group consisting of increased expression of a target protein, inhibition of lactate production, regulation of histone protein deacetylation, regulation of glucose metabolism, regulation of cell growth, proliferation regulation, increased functionality of a target protein, and decreased fucose content of a target protein, through intron splicing or endogenous gene expression regulation.

Figure 8:
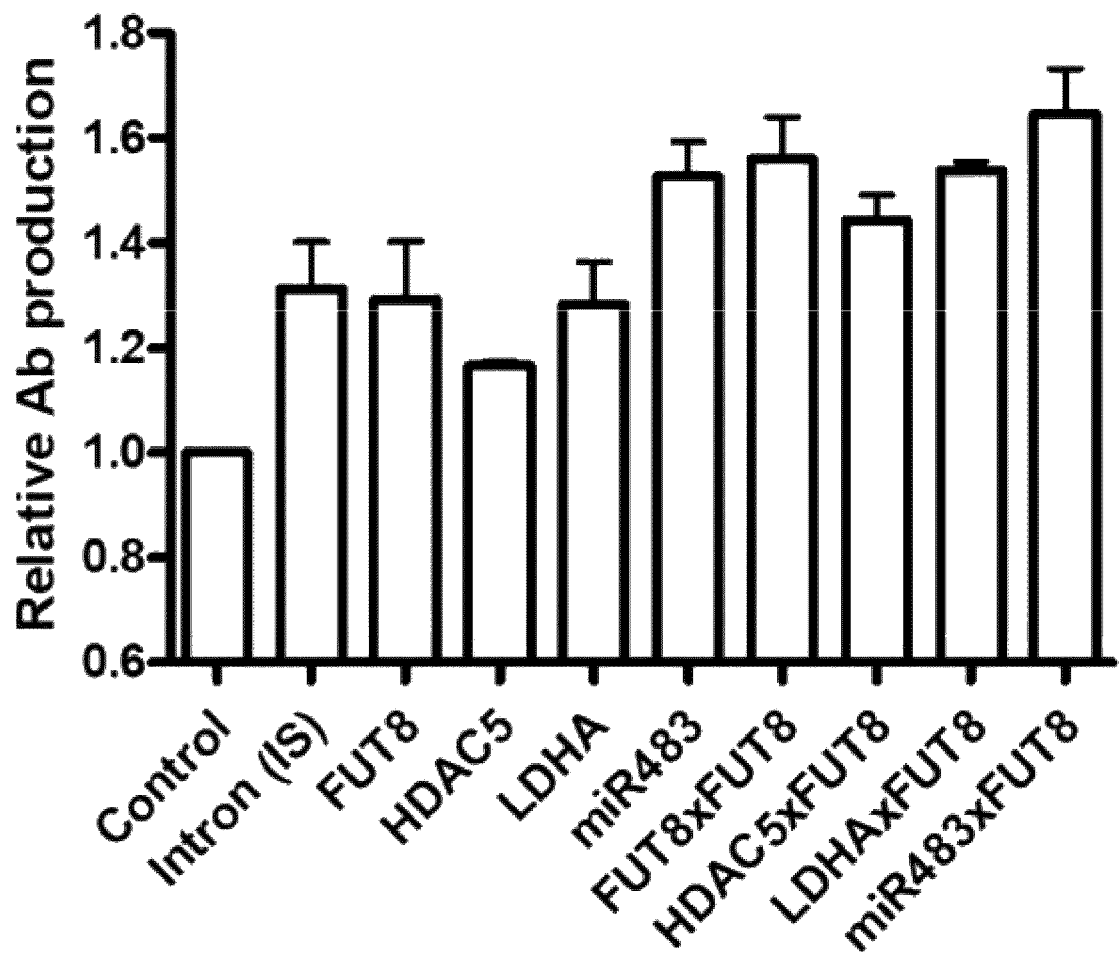
FIG. 8 is a graph showing the results of comparison of antibody production levels for a short time through transient expression after transfection with an intron-free antibody expression vector (control), an antibody expression vector including an intron sequence (IS) having no endogenous gene regulation function, and an antibody expression vector including intronic shRNA/miRNA for endogenous gene regulation.
Figure 9:
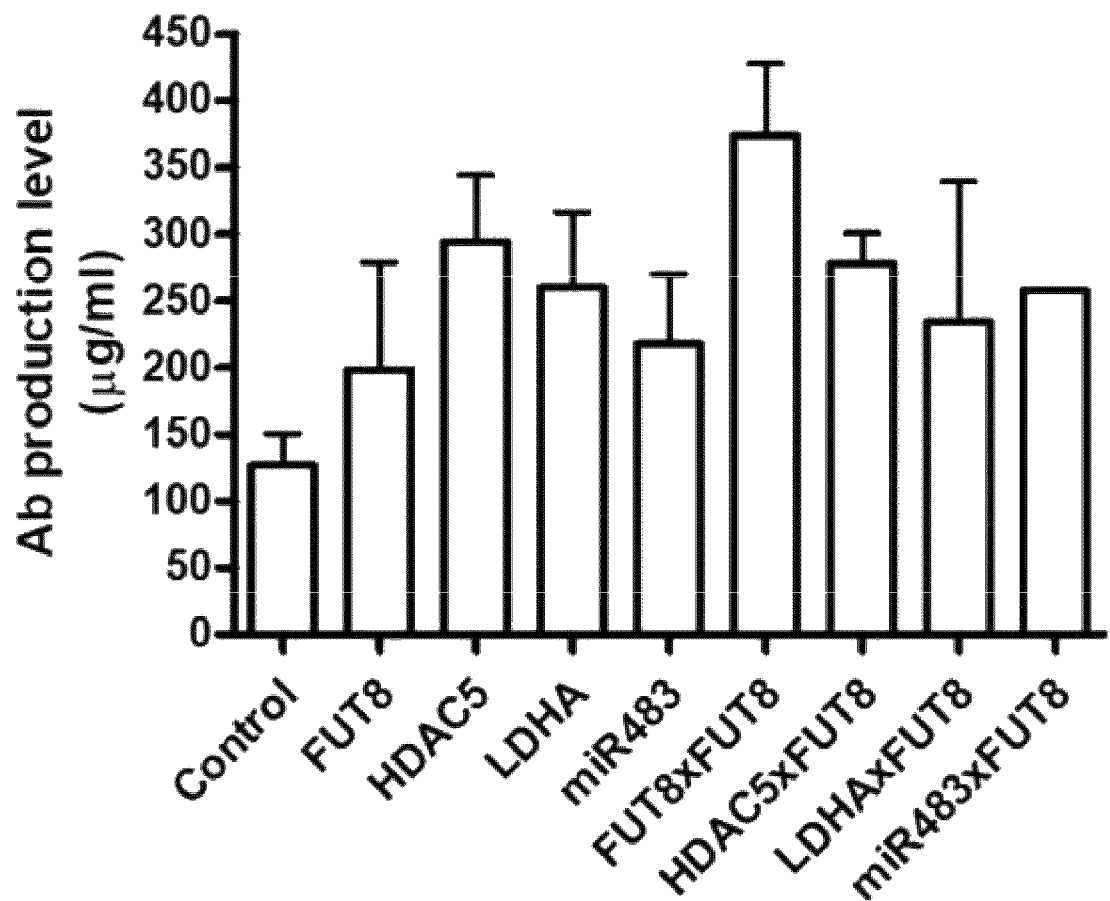
FIG. 9 is a graph showing the results of measurement of antibody production levels after respective stable cell lines are manufactured by transfection with an intron-free antibody expression vector (control) and an antibody expression vector including intronic shRNA/miRNA for endogenous gene regulation.

In an embodiment of the present invention, as shown in FIGS. 8 and 9, it was confirmed that more antibodies are produced in transformants including intronic RNA than transformants not including intronic RNA. Particularly, when two or more intronic RNAs were included, it was confirmed that higher antibody productivity was exhibited (FIGS. 8 and 9).

The expression cassette may regulate the expression of the target endogenous gene using the intronic RNA sequence for endogenous gene regulation. The regulation of gene expression includes a method of increasing or decreasing a gene expression level. The expression cassette is configured such that an intronic RNA sequence and a target protein are transcriptionally linked by a single promoter, and thus, even when a cell line is selected by checking only the expression of the target protein, it is possible to select a cell line in which the endogenous gene is regulated by intronic RNA.

Figure 10:
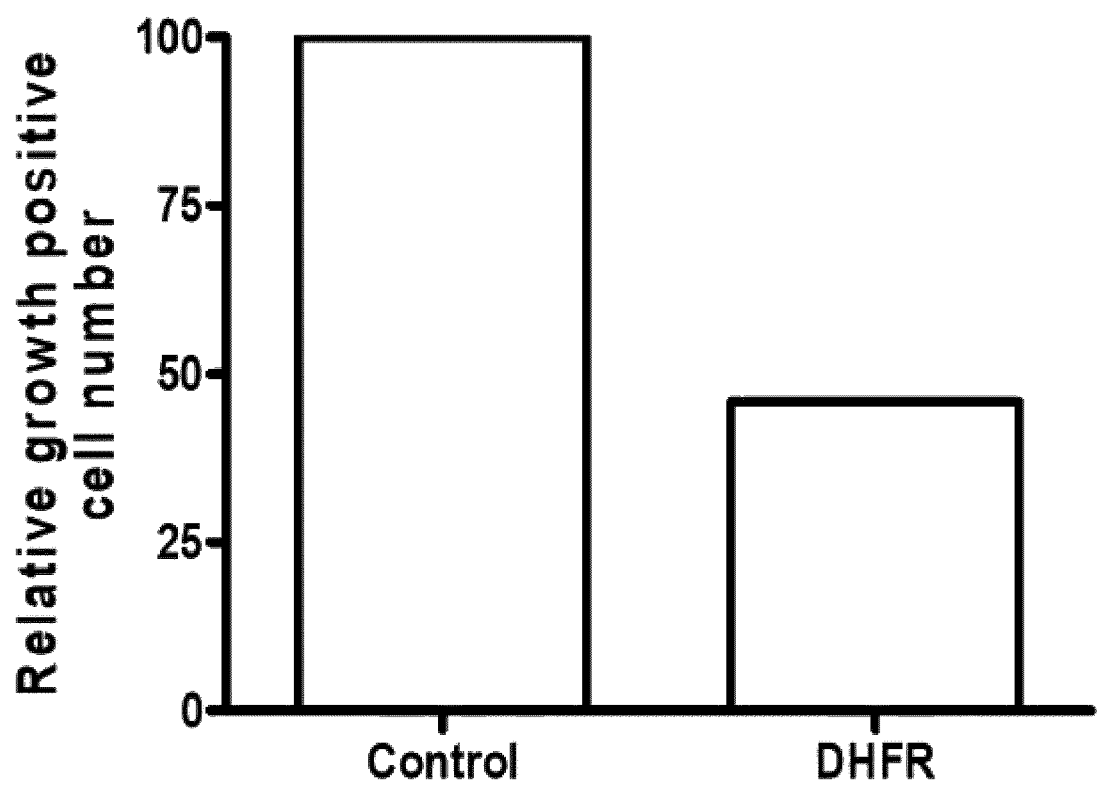
FIG. 10 is a graph showing the results of measurement of the number of stable cell lines selected using methotrexate (mTX) after transfection with an antibody expression vector including intronic shRNA for DHFR regulation.
Figure 11A:
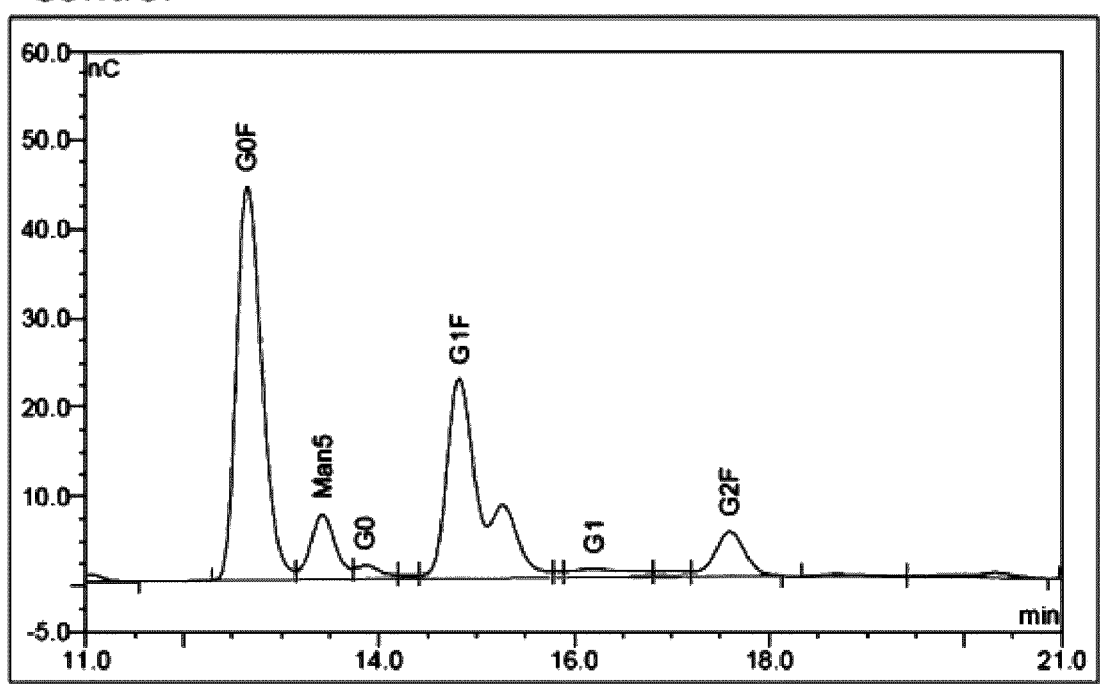
FIGS. 11a to 11f show the results of analysis of the glycan of the antibody produced in a stable cell line using Bio-LC after transfection with an antibody expression vector including intronic shRNA for endogenous gene regulation (a: control, b: test group including FUT8 intronic shRNA, c: test group including two FUT8 intronic shRNAs, d: test group including both MACS and FUT8 shRNA, e: test group including both LDHA and FUT8 shRNA, f: test group including both miR483 miRNA and FUT8 shRNA)
Figure 11B:
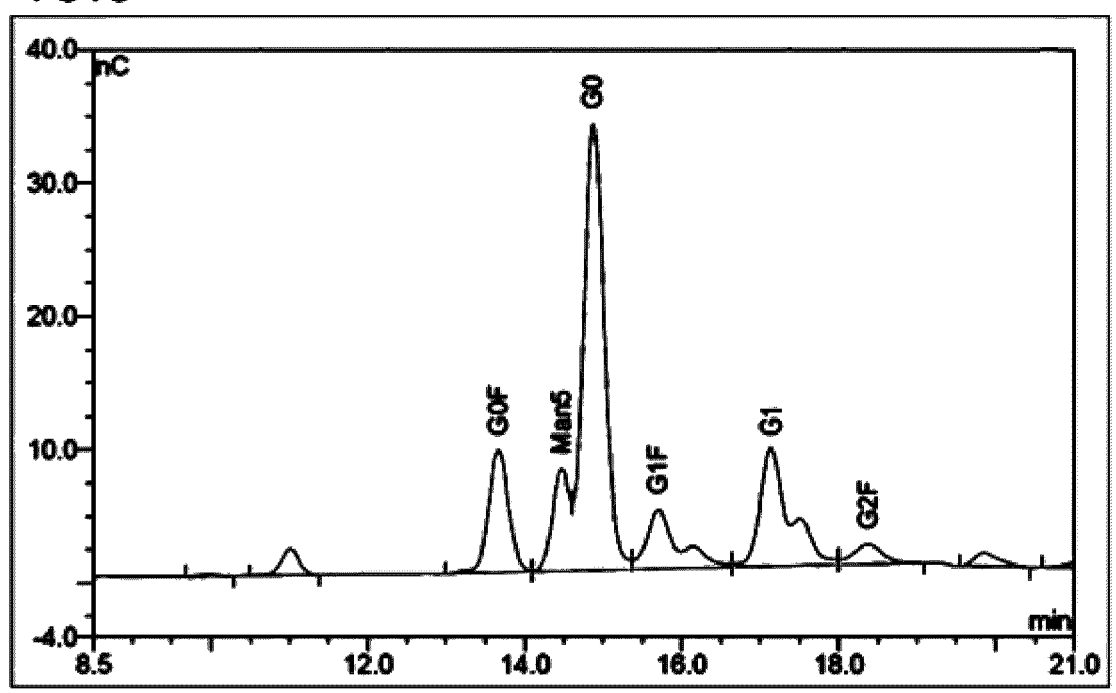
Figure 11C:
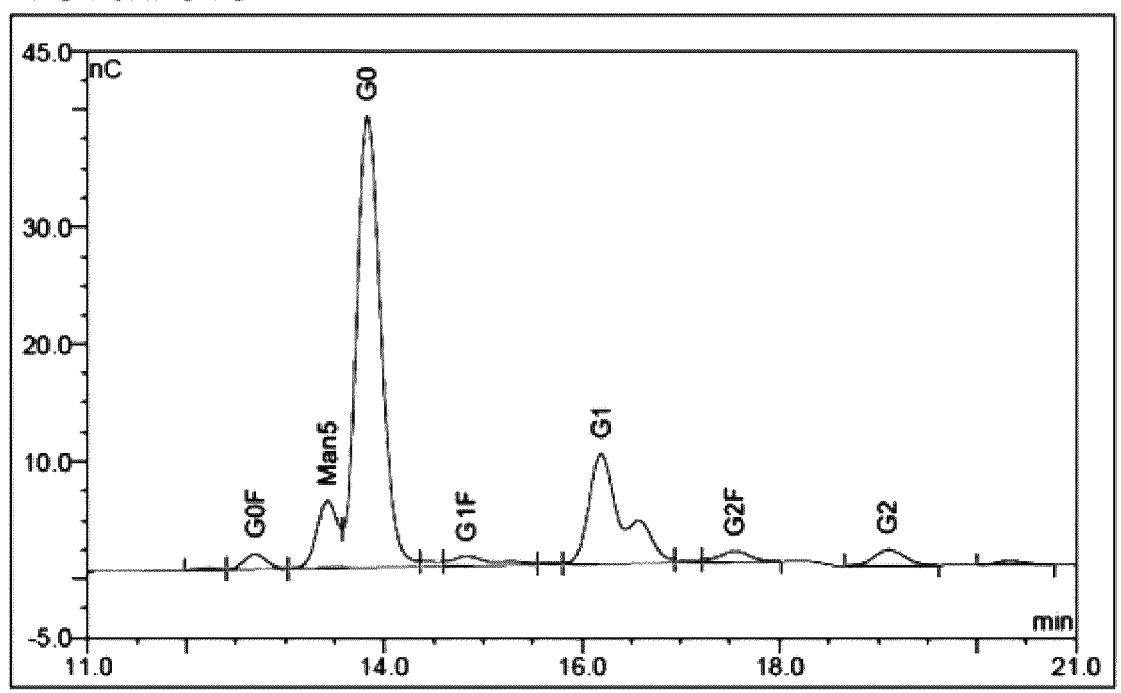
Figure 11D:
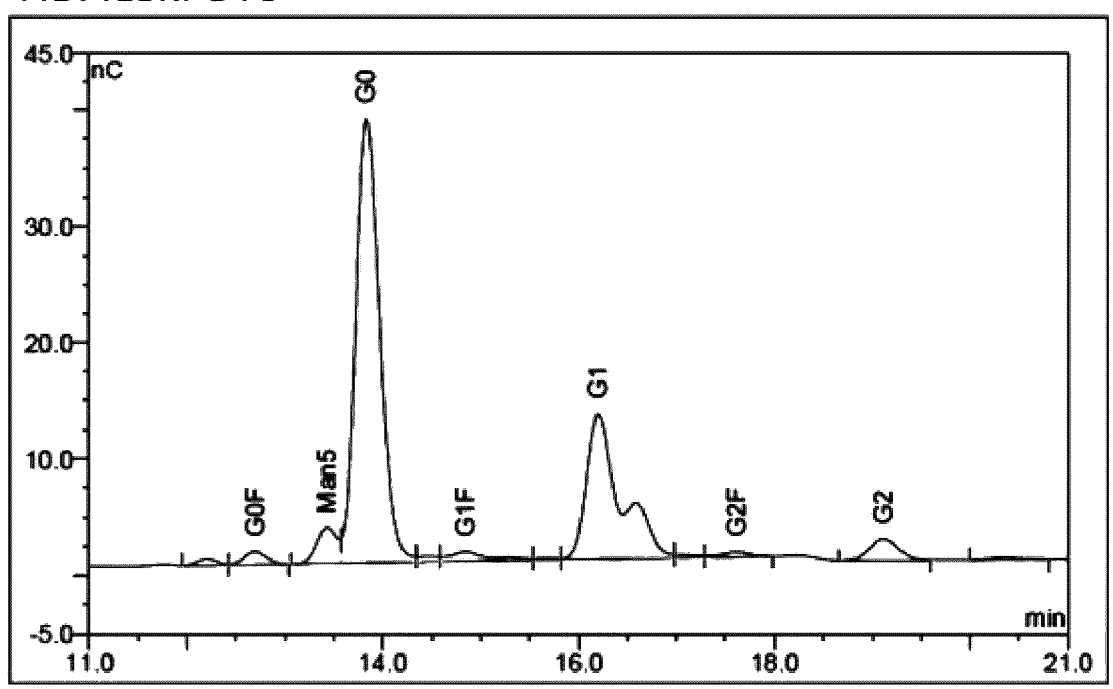
Figure 11E:
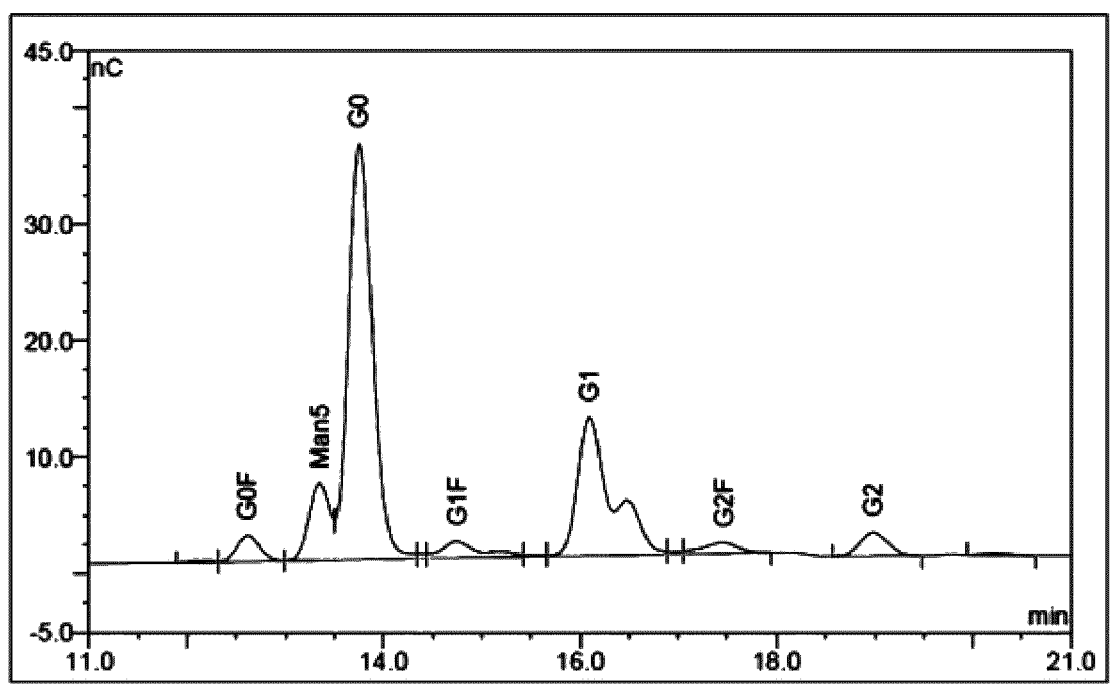
Figure 11F:
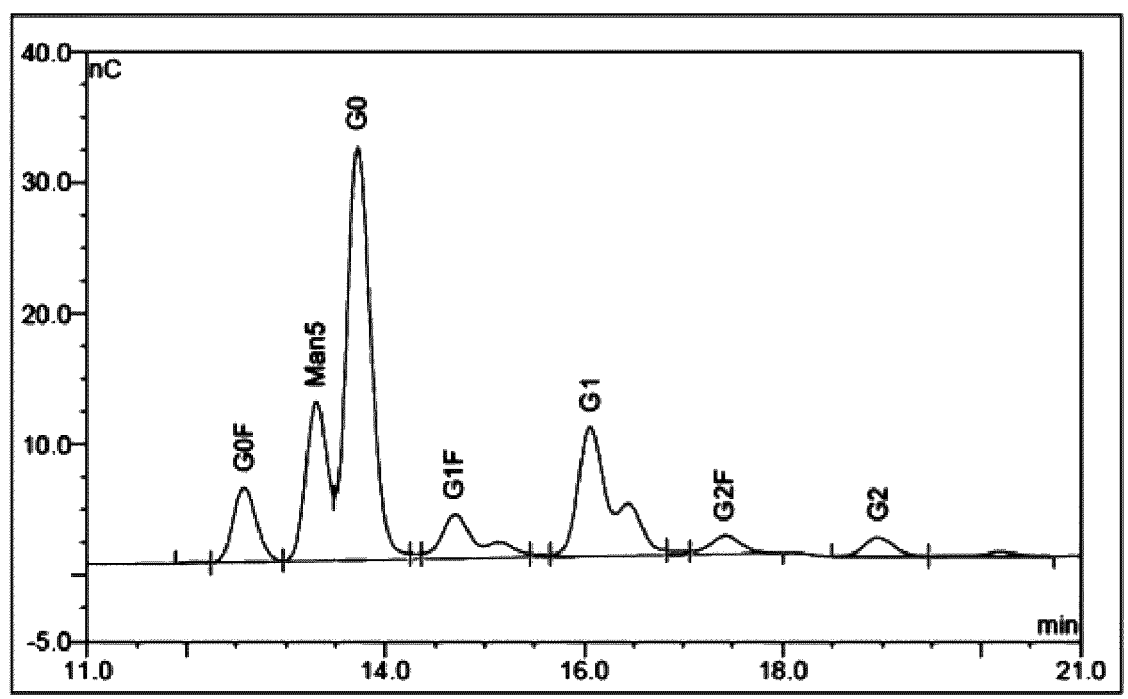

In an exemplary embodiment of the present invention, it was confirmed that a small number of cell lines grew when selecting cell lines with DHFR as a selection marker by inhibiting the expression of dihydrofolate reductase (DHFR), which is an enzyme involved in the conversion of dihydrofolate into tetrahydrofolate (FIG. 10).

In an exemplary embodiment of the present invention, it was confirmed that the fucose content of the antibody expressed by the same promoter was decreased by regulating the expression of alpha 1,6-fucosyltransferase (FUT8), which is an enzyme related to fucosylation of the N-linked glycan of asparagine 297, which is the Fc region of the antibody (FIG. 11).

In an exemplary embodiment of the present invention, it was confirmed that the expression of histone deacetylase was decreased by regulating the expression of histone deacetylase 5 (HDAC5), which is involved in deacetylation of histone protein (FIG. 12a).

In an exemplary embodiment of the present invention, it was confirmed that the expression of lactate dehydrogenase A was decreased by regulating the expression of lactate dehydrogenase A (LDHA), which is an enzyme involved in the conversion of pyruvate into lactate (FIG. 12b).

In an exemplary embodiment of the present invention, it was confirmed that the expression of CXCR4 was increased and the expression of PDK4 was decreased by regulating the expression of CXCR4, PDK4, MAPK3 and KANK4 using miR483 (FIGS. 12c and 12d).

In addition, the present invention pertains to a vector including the expression cassette for production of a target protein.

In addition, the present invention pertains to a transformant, which is transformed with the vector including the expression cassette for production of a target protein. The transformant is not limited, so long as it is able to produce a target protein, and is preferably an animal cell.

In an embodiment of the present invention, the transformant may be a eukaryotic cell. The eukaryotic cell is preferably a mammalian cell. More preferably, the mammalian cell is selected from among a CHO (Chinese hamster ovary) cell, BHK (baby hamster kidney) cell, mouse myeloma cell, rat myeloma cell, hybridoma cell, embryonic stem cell, fertilized egg cell, CHO-K1 cell, CHO DUXB11 cell, CHO DG44 cell, N50 cell, NS0 cell, SP2/0 cell, YB2 cell, HEK 293 cell, HEK 293 EBNA cell, PER.C6 cell, Namalwa cell, and COS cell.

In addition, the present invention pertains to a method of manufacturing a target protein including culturing a transformant including the expression cassette for production of a target protein.

More specifically, the method of manufacturing a target protein according to the present invention may include transfecting an animal cell with a vector in which an intron sequence for endogenous gene regulation and a target protein are expressed by a single promoter, culturing the transfected animal cell under conditions suitable for the expression of the target protein, and recovering a target protein from the animal cell or cell culture broth.

A better understanding of the present invention will be given through the following examples. Here, these examples are set forth to illustrate the present invention, and are not to be construed as limiting the scope of the present invention.

Example 1. Manufacture of Intron Sequence

By appropriately combining a splicing donor (SD), a gene target shRNA sequence, a branch sequence and a splicing acceptor (SA) nucleotide sequence, a new intron DNA sequence capable of being spliced was completed and manufactured through synthesis, as shown in Table 1 below.

TABLE 1

| No. | Classification | Construction of intron sequence | SEQ ID NO: |
|---|---|---|---|
| 1 | Intron (IS) | SD + branch + SA | 23 |
| 2 | FUT8 | SD + FUT8 target shRNA + branch + SA | 24 |
| 3 | HDAC5 | SD + HDAC5 target shRNA + branch + SA | 25 to 27 |
| 4 | LDHA | SD + LDHA target shRNA + branch + SA | 28 to 30 |
| 5 | DHFR | SD + DHFR target shRNA + branch + SA | 31 to 33 |
| 6 | miR483 | SD + miR483 target miRNA + branch + SA | 34 to 36 |

No. 1 intron (IS) in Table 1 did not insert a gene target shRNA, or inserted a shRNA sequence having no gene expression regulation function, so that a splicing effect occurred only in the gene DNA. Also, in the case of No. 2 to 5 introns, intron DNA sequences were manufactured by inserting a polynucleotide sequence encoding shRNA to induce the inhibition of expression of each gene. Finally, No. 6 intron was manufactured in order to evaluate whether miRNA, rather than shRNA, was applicable to the present invention.

Example 2. Manufacture of Expression Cassette

As shown in FIG. 1, an expression cassette capable of simultaneously expressing an intronized shRNA sequence and a target protein was designed by inserting a polynucleotide sequence encoding at least one intronic shRNA sequence into a single expression cassette expressing a target protein. The expression cassette was synthesized by requesting GeneArt by combining a splicing donor, a gene target shRNA or miRNA sequence, a branch sequence and a splicing acceptor nucleotide sequence. Both ends of the synthesized DNA sequence were added with HpaI/NheI or ClaI restriction enzyme sites through PCR and then cloned into an expression cassette composed of a CMV (cytomegalovirus) promoter+Palivizumab light chain+poly A. The final expression cassette was manufactured through cloning between the CMV promoter and the Palivizumab light chain using HpaI and NheI restriction enzymes and between the Palivizumab light chain and poly A using a ClaI restriction enzyme.

The configuration of the specific expression cassette is shown in FIG. 2 and in Table 2 below.

TABLE 2

| No. | Classification | Construction of expression cassette |
|---|---|---|
| 1 | Control | Promoter + target protein expression gene (hereinafter, gene of interest (GOI)) + poly A |
| 2 | Intron (IS) | Promoter + intron (IS) + GOI + poly A |
| 3 | FUT8 | Promoter + FUT8 target intronic shRNA + GOI + poly A |
| 4 | HDAC5 | Promoter + HDAC5 target intronic shRNA + GOI + poly A |
| 5 | LDHA | Promoter + LDHA target intronic shRNA + GOI + poly A |
| 6 | miR483 | Promoter + miR483 intronic miRNA + GOI + poly A |
| 7 | DHFR | Promoter + GOI + DHFR target intronic shRNA + poly A |
| 8 | FUT8 × FUT8 | Promoter + FUT8 target intronic shRNA + GOI + FUT8 target intronic shRNA + poly A |
| 9 | HDAC5 × FUT8 | Promoter + HDAC5 target intronic shRNA + GOI + FUT8 target intronic shRNA + poly A |
| 10 | LDHA × FUT8 | Promoter + LDHA target intronic shRNA + GOI + FUT8 target intronic shRNA + poly A |
| 11 | miR483 × FUT8 | Promoter + miR483 intronic miRNA + GOI + FUT8 target intronic shRNA + poly A |

Nos. 3 to 5 in Table 2 were designed in order to evaluate whether the insertion of shRNA before GOI affects the expression of each target gene. No. 7 was designed to test the case in which shRNA was inserted after GOI, and Nos. 8 to 11 were manufactured in order to evaluate whether the effect of the present invention is exhibited even when two or more shRNA-shRNA combinations or shRNA-miRNA combinations are included before and after GOI.

Example 3. Vector Cloning

A MarEx vector (Korean Patent No. 10-1076602) having dihydrofolate reductase (DHFR) as a selection marker was cloned with the heavy and light chain genes of Palivizumab, serving as a therapeutic agent for preventing respiratory syncytial virus infection, after which an intron sequence or at least one intronic shRNA/miRNA sequence for endogenous gene regulation (Tables 1 and 2) was inserted into the light-chain expression cassette of the MarEx vector in which Palivizumab was expressed. After transformation with E. coli (DH5alpha), a plasmid was obtained. The sequence of the MarEx vector including the intron sequence or at least one intronic shRNA/miRNA sequence for endogenous gene regulation and the antibody sequence was identified, thus obtaining a final vector, and plasmid DNA was obtained using an Endo-free Plasmid Maxi Kit (Qiagen).

Example 4. Evaluation of Endogenous Gene Regulation Through Transient Expression

Example 4-1. Evaluation of HDAC5 Expression Regulation

An inhibitory intron shRNA1 (SEQ ID NO: 25) targeting a sequence 626 bp of HDAC5 in Example 3, an inhibitory intron shRNA2 (SEQ ID NO: 26) targeting a sequence 823 bp of HDAC5, and an inhibitory intron shRNA3 (SEQ ID NO: 27) targeting a sequence 2326 bp of HDAC5 were manufactured. Thereafter, whether the expression of HDAC5 was inhibited in cells was evaluated through transient expression.

In order to confirm the expression of the gene, cells were obtained, and total RNA was extracted using an RNeasy Mini Kit (Qiagen). Analysis was performed through real-time PCR after reverse transcription and cDNA synthesis using a one-step SYBR PrimeScript RT-PCR Kit II (Ta-KaRa) with an equivalent amount of total RNA (100 ng). For amplification and detection of HDAC5 and GAPDH cDNA, GAPDH primers represented by SEQ ID NOS: 37 and 38 and HDAC5 primers represented by SEQ ID NOS: 39 and 40 were used.

Using an Applied Biosystems 7500 Real-Time PCR System, reverse transcription at 42° C. for 5 min and at 95° C. for 10 min and amplification of 40 cycles at 95° C. for 5 sec and at 60° C. for 34 sec were performed, whereby the HDAC5 cDNA level was normalized to the level of the housekeeping gene GAPDH. Consequently, as shown in FIG. 3, the effect of inhibiting the expression of HDAC5 was confirmed in all HDAC5 shRNA sequences, among which HDAC5 shRNA3 represented by SEQ ID NO: 27 inhibited the expression of HDAC5 by 37% compared to the control and was thus found to be the most effective.

Example 4-2. Evaluation of LDHA Expression Regulation

An inhibitory intron shRNA1 (SEQ ID NO: 28) targeting a sequence 273 bp of LDHA in Example 3, an inhibitory intron shRNA2 (SEQ ID NO: 29) targeting a sequence 473 bp of LDHA, and an inhibitory intron shRNA (SEQ ID NO: 30) targeting a sequence 906 bp of LDHA were manufactured. Thereafter, whether the expression of LDHA was inhibited in cells was evaluated through transient expression.

The expression of the gene was confirmed in the same manner as in Example 4-1, and for amplification and detection of GAPDH and LDHA cDNA, GAPDH primers represented by SEQ ID NOS: 37 and 38 and LDHA primers represented by SEQ ID NOS: 41 and 42 were used.

Consequently, as shown in FIG. 4, the effect of inhibiting the expression of LDHA was confirmed in all LDHA shRNA sequences, among which LDHA shRNA3 represented by SEQ ID NO: 30 inhibited the expression of LDHA by 68.9% compared to the control and was thus found to be the most effective.

Example 4-3. Evaluation of DHFR Expression Regulation

An inhibitory intron shRNA1 (SEQ ID NO: 31) targeting a sequence 41 bp of DHFR in Example 3, an inhibitory intron shRNA2 (SEQ ID NO: 32) targeting a sequence 307 bp of DHFR, and an inhibitory intron shRNA (SEQ ID NO: 33) targeting a sequence 323 bp of DHFR were manufactured. Thereafter, whether the expression of DHFR was inhibited in cells was evaluated through transient expression.

The expression of the gene was confirmed in the same manner as in Example 4-1, and for amplification and detection of GAPDH and DHFR cDNA, GAPDH primers represented by SEQ ID NOS: 37 and 38 and DHFR primers represented by SEQ ID NOS: 47 and 48 were used.

Consequently, as shown in FIG. 5, the effect of inhibiting the expression of DHFR was confirmed, among which DHFR shRNA2 represented by SEQ ID NO: 32 inhibited the expression of DHFR by 58.8% compared to the control and was thus found to be the most effective.

Example 4-4. Evaluation of CXCR4 and PDK4 Expression Regulation Through miR483 Expression As intron sequences for inducing the expression of miR483 in Example 3, miR483 1 (SEQ ID NO: 34), miR483 2 (SEQ ID NO: 35) and miR483 3 (SEQ ID NO: 36) were manufactured. Thereafter, the effects of increasing the expression of CXCR4 (C—X—C chemokine receptor type 4), which is a target of mi483, and inhibiting the expression of PDK4 (pyruvate dehydrogenase kinase 4) were measured through transient expression.

The expression of the gene was confirmed in the same manner as in Example 4-1, and for amplification and detection of GAPDH, CXCR4 and PDK4 cDNA, GAPDH primers represented by SEQ ID NOS: 37 and 38, CXCR4 primers represented by SEQ ID NOS: 43 and 44 and PDK4 primers represented by SEQ ID NOS: 45 and 46 were used.

Consequently, as shown in FIG. 6, miR483 3 represented by SEQ ID NO: 36 increased the expression of CXCR4 by 270.4% or more compared to the control, and as shown in FIG. 7, miR483 3 represented by SEQ ID NO: 36 inhibited the expression of PDK4 by 23.2% compared to the control.

Example 5. Manufacture of Expression Cell Line

Using the vectors manufactured in Example 3, a stable cell line in which an antibody and an intron sequence or at least one intronic shRNA/miRNA for endogenous gene regulation were transcribed and expressed was manufactured.

Specifically, a CHO-K1 (American Type Culture Collection, CCL-61, USA) cell was transfected with the above vector using Lipofectamine LTX (Invitrogen), and was then treated with 500 nM methotrexate (MTX) serving as a DHFR inhibitor in order to select the stably transfected cell line, thereby manufacturing a cell line in which the antibody was stably expressed.

Example 6. Evaluation of Antibody Production and Expression Level

Example 6-1. Evaluation of Antibody Production Level for Short Time Through Transient Expression After transfection with an intron-free antibody expression vector (control), an antibody expression vector including an intron sequence (IS) having no endogenous gene regulation function, and an antibody expression vector including an intronic shRNA/miRNA sequence for endogenous gene regulation, the antibody production level was measured for a short time through transient expression.

The antibody production level was measured using an enzyme-linked immunosorbent assay (ELISA) technique specific to the Fc region of the antibody.

Consequently, as shown in FIG. 8 and in Table 3 below, in the cell line including the intron sequence having no endogenous gene regulation function, the antibody production level was 1.3 times higher than that of the control. Moreover, in the cell line including the intron sequence for endogenous gene regulation, the antibody production level was increased up to 1.8 times.

TABLE 3

| No. | Classification | Relative antibody production level compared to control |
|---|---|---|
| 1 | Control | 1.00 times |
| 2 | Intron (IS) | 1.31 times |
| 3 | FUT8 | 1.29 times |
| 4 | HDAC5 | 1.17 times |
| 5 | LDHA | 1.28 times |
| 6 | miR483 | 1.53 times |
| 7 | FUT8 × FUT8 | 1.56 times |
| 8 | HDAC5 × FUT8 | 1.44 times |
| 9 | LDHA × FUT8 | 1.54 times |
| 10 | miR483 × FUT8 | 1.65 times |

Example 6-2. Evaluation of Antibody Expression Level in Stabilized Cell Line

After transfection with an intron-free antibody expression vector (control) and an antibody expression vector including intronic shRNA/miRNA for endogenous gene regulation, stable cell lines were manufactured, and then the antibody production levels thereof were measured.

The antibody production level was measured using an enzyme-linked immunosorbent assay (ELISA) technique specific to the Fc region of the antibody.

Consequently, as shown in FIG. 9 and in Table 4 below, in the cell line including the intron sequence for endogenous gene regulation, the antibody expression level was increased in the range from 1.57 times to 2.95 times.

TABLE 4

| No. | Classification | Antibody expression level | Relative antibody expression level compared to control |
|---|---|---|---|
| 1 | Control | 126.6 µg/ml | 1.00 times |
| 2 | FUT8 | 198.5 µg/ml | 1.57 times |
| 3 | HDAC5 | 293.8 µg/ml | 2.32 times |
| 4 | LDHA | 260.1 µg/ml | 2.05 times |
| 5 | miR483 | 217.7 µg/ml | 1.72 times |
| 6 | FUT8 × FUT8 | 374.0 µg/ml | 2.95 times |
| 7 | HDAC5 × FUT8 | 277.8 µg/ml | 2.19 times |
| 8 | LDHA × FUT8 | 234.3 µg/ml | 1.85 times |
| 9 | miR483 × FUT8 | 257.6 µg/ml | 2.03 times |

Example 7. Evaluation of Reduction of Selected Cell Line

After transfection with an intron-free antibody expression vector (control) and an antibody expression vector including intronic shRNA for DHFR inhibition and then treatment with methotrexate (MTX) for inhibition of the expression of DHFR, a cell line selection process was performed.

Consequently, as shown in FIG. 10, it was confirmed for the cell line transfected with the vector including intronic shRNA for DHFR inhibition that the cell line showing 54.1% less expression than the control was selected. Thus, a high-expression cell line can be identified using only a small number of cell lines.

Example 8. Evaluation of Fucose Content of Antibody

The antibody was purified from the cell line manufactured in Example 5, after which the glycan of the Fc region was analyzed using a Bio-LC system (DC ICS 3000 System, DIONEX, 06110276). The purified antibody was heated at 100° C. for 4 hr using 4 M TFA (Trifluoroacetic acid) to separate monosaccharides, and the filtrate was removed using a vacuum dryer, dissolved in deionized water and measured using a Bio-LC system. For the measurement, an ED detector (DIONEX, 06110046) was used, and an amino trap column (DIONEX, 046122) was used as a guard column. Additionally, a CarboPac PA 10 column (DIONEX, 046110) was used as an analytical column. The analysis results through Bio-LC are shown in FIG. 11, and the area ratio of each peak was quantified, and is shown in Table 5 below.

TABLE 5

| % Area/Total area | G0F | Man5† | G0 | G1F | G1 | G2F | G2 | Non-fucosylated ratio (G0 + G1 + G2) | Compared to control |
|---|---|---|---|---|---|---|---|---|---|
| Control | 57.14 | 5.65 | 1.7 | 27.55 | 2.41 | 5.54 | — | 4.11 | — |
| FUT8 | 12.66 | 8.72 | 47.72 | 9.64 | 18.2 | 3.06 | — | 65.9 | 16.0 times |
| FUT8 × FUT8 | 1.89 | 7.66 | 61.9 | 2.4 | 21.45 | 1.98 | 2.71 | 86.1 | 20.9 times |
| HDAC5 × FUT8 | 1.64 | 4.02 | 59.99 | 2.27 | 27.79 | 0.88 | 3.41 | 91.2 | 22.2 times |
| LDHA × FUT8 | 3.18 | 8.45 | 53.51 | 3.54 | 25.55 | 2.17 | 3.59 | 82.7 | 20.1 times |
| miR483 × FUT8 | 7.75 | 14.99 | 44.55 | 7.33 | 20.27 | 2.58 | 2.53 | 67.4 | 16.4 times |

* G0F, G1F and G2F: binding forms of fucose
†Man5: glycan form before the formation of G0, G1 or G2, etc., so it is not summed to the ratio of non-glycosylated fucose In the cell line including the FUT8 intron sequence, the proportion of the antibody to which fucose was not bound was 16.0 times that of the control. Also, in the cell line including the FUT8×FUT8 intron sequence, it was confirmed that the proportion of the antibody to which fucose was not bound was 20.9 times that of the control.

Moreover, in the cell lines respectively including the HDAC5×FUT8 FUT8 intron sequence, LDHA×FUT8 intron sequence and miR483×FUT8 intron sequence, the proportions of the antibody to which fucose was not bound were 22.2 times, 20.1 times and 16.4 times that of the control, respectively.

Example 9. Evaluation of Endogenous Gene Regulation Through Stable Cell Line

Example 9-1. Evaluation of HDAC5 Expression Regulation

Using the stable cell line manufactured in Example 5, whether the expression of HDAC5 was inhibited in cells was evaluated. In order to confirm the expression of the gene, cells were obtained, and total RNA was extracted using an RNeasy Mini Kit (Qiagen). Analysis through real-time PCR after reverse transcription and cDNA synthesis using a one-step SYBR PrimeScript RT-PCR Kit II (TaKaRa) with an equivalent amount of total RNA (100 ng) was performed. For amplification and detection of HDAC5 and GAPDH cDNA, GAPDH primers represented by SEQ ID NOS: 37 and 38 and HDAC5 primers represented by SEQ ID NOS: 39 and 40 were used.

Using an Applied Biosystems 7500 Real-Time PCR System, reverse transcription at 42° C. for 5 min and at 95° C. for 10 min and amplification of 40 cycles at 95° C. for 5 sec and at 60° C. for 34 sec were performed, whereby the HDAC5 cDNA level was normalized to the level of the housekeeping gene GAPDH.

Figure 12:
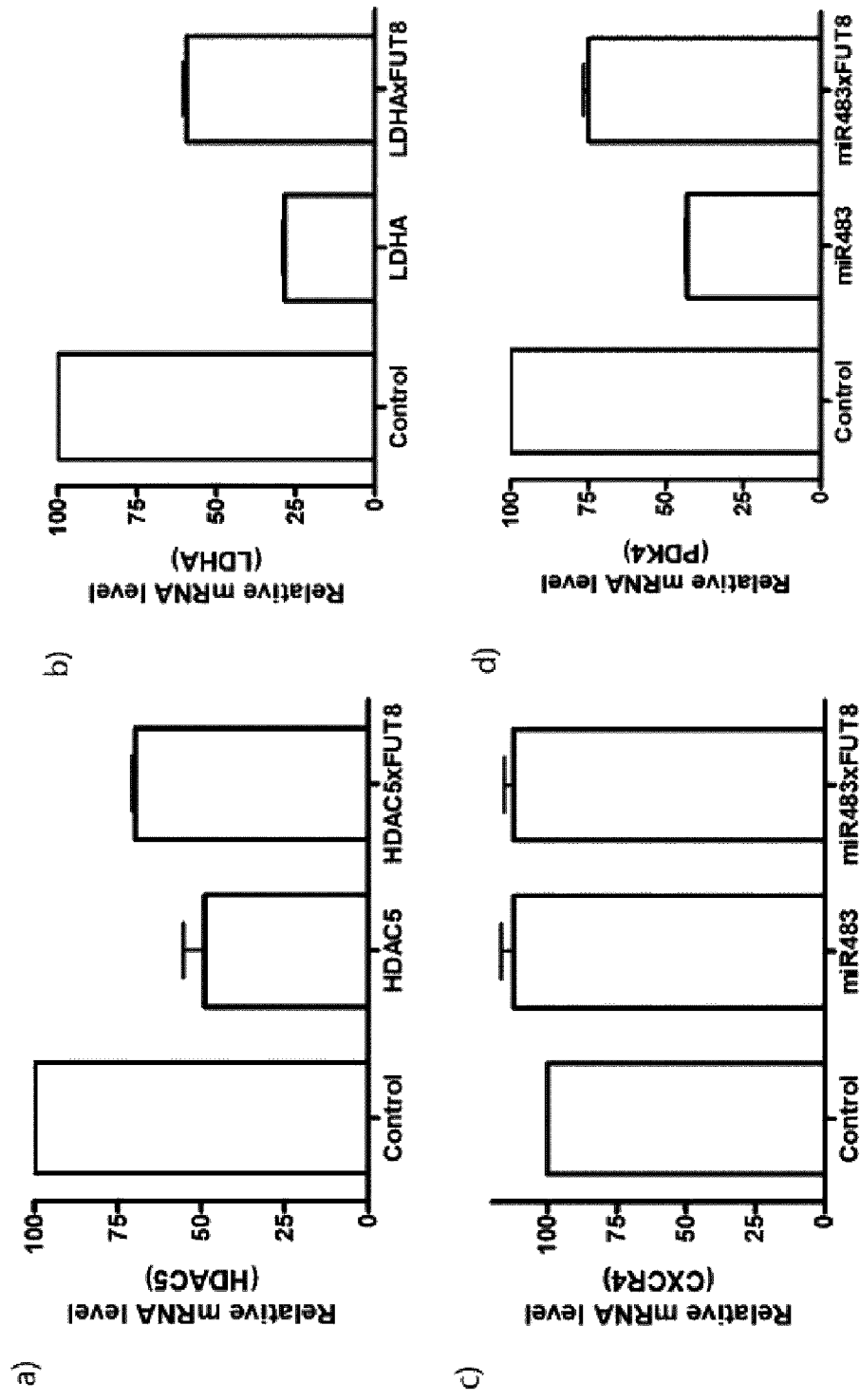
FIG. 12 is a graph showing the results of measurement of the amount of mRNA of an endogenous gene (a: MACS, b: LDHA, c: CXCR4 and d: PDK4) using a quantitative RT-PCR process after a stable cell line is manufactured by transfection with an antibody expression vector including intronic shRNA/miRNA for endogenous gene regulation.

Consequently, as shown in FIG. 12 *a*), in the stable cell lines for HDAC5 and HDAC5×FUT8 expression regulation, the expression levels of HDAC5 were inhibited by 51.0% and 30.2% compared to the control, respectively.

Example 9-2. Evaluation of LDHA Expression Regulation

Using the stable cell line manufactured in Example 5, whether the expression of LDHA was inhibited in cells was evaluated. The gene regulation was confirmed in the same manner as in Example 9-1, and for amplification and detection of GAPDH and LDHA cDNA, GAPDH primers represented by SEQ ID NOS: 37 and 38 and LDHA primers represented by SEQ ID NOS: 41 and 42 were used.

Consequently, as shown in FIG. 12 *b*), in the stable cell lines for LHDA and LDHA×FUT8 expression regulation, the expression levels of LDHA were inhibited by 71.52% and 40.5% compared to the control, respectively.

Example 9-3. Evaluation of CXCR4 and PDK4 Expression Regulation Through miR483 Expression Using the stable cell line manufactured in Example 5, the effects of increasing the expression of CXCR4 as a target of miR483 and inhibiting the expression of PDK4 were evaluated. The gene regulation was confirmed in the same manner as in Example 9-1, and for amplification and detection of GAPDH, CXCR4 and PDK4 cDNA, GAPDH primers represented by SEQ ID NOS: 37 and 38, CXCR4 primers represented by SEQ ID NOS: 43 and 44 and PDK4 primers represented by SEQ ID NOS: 45 and 46 were used.

Consequently, as shown in FIG. 12 *c*), in the stable cell lines for miR483 and miR483×FUT8 expression regulation, the expression of CXCR4 was increased by 112.2% or more compared to the control. Also, as shown in FIG. 12 *d*), the expression levels of PDK4 as another target were inhibited by 56.9% and 25.1% compared to the control, respectively.

The invention claimed is:

1. An expression cassette for production of a target protein, comprising a single promoter, a polynucleotide coding for the target protein, a poly A sequence, and a polynucleotide sequence encoding an intronic RNA sequence, wherein the intronic RNA sequence comprises a splicing donor, a branch, a splicing acceptor, and a target gene expression regulation RNA sequence;

wherein the target protein is an antibody or a fragment thereof;

wherein the single promoter transcriptionally links the polynucleotide coding for the target protein and the polynucleotide sequence encoding the intronic RNA;

and wherein the target gene expression regulation RNA sequence comprises one or more shRNA (small hairpin RNA) sequences selected from the group consisting of intronic FUT8 (Alpha-1,6-fucosyltransferase) shRNA represented by SEQ ID NO: 24, intronic HDAC5 (histone deacetylase 5) shRNA represented by any one of SEQ ID NOS: 25 to 27, intronic LDHA (lactate dehydrogenase A) shRNA represented by any one of SEQ ID NOS: 28 to 30, and intronic DHFR (dihydrofolate reductase) shRNA represented by any one of SEQ ID NOS: 31 to 33.

2. The expression cassette for production of a target protein of claim 1, wherein the target gene expression regulation RNA sequence comprises intronic FUT8 shRNA represented by SEQ ID NO: 24.

3. The expression cassette for production of a target protein of claim 1, wherein the splicing donor comprises one or more sequence selected from among SEQ ID NOS: 12 to 15, the branch comprises one or more sequence selected from among SEQ ID NOS: 16 to 18, and the splicing acceptor comprises one or more sequence selected from among SEQ ID NOS: 19 to 22.

4. The expression cassette for production of a target protein of claim 1, wherein antibody expression level of an expression cell line comprising the expression cassette for production of a target protein is 198.5 ug (micrograms)/ml (milliliters) to 374.0 ug/ml.

5. A vector comprising the expression cassette for production of a target protein of claim 1.

6. The expression cassette for production of a target protein of claim 1, wherein the target gene expression regulation RNA sequence comprises intronic HDAC5 (histone deacetylase 5) shRNA represented by any one of SEQ ID NOs: 25 to 27.

7. The expression cassette for production of a target protein of claim 1, wherein the target gene expression regulation RNA sequence comprises intronic LDHA (lactate dehydrogenase A) shRNA represented by any one of SEQ ID NOs: 28 to 30.

8. The expression cassette for production of a target protein of claim 1, wherein the target gene expression regulation RNA sequence comprises and intronic DHFR (dihydrofolate reductase) shRNA represented by any one of SEQ ID NOs: 31 to 33.

* * * * *